(12) United States Patent
Hendricks et al.

(10) Patent No.: US 10,494,671 B2
(45) Date of Patent: Dec. 3, 2019

(54) ENZYMATIC LIGATION OF NUCLEIC ACIDS

(75) Inventors: Stephen Hendricks, Los Gatos, CA (US); David King, San Francisco, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 192 days.

(21) Appl. No.: 13/980,280

(22) PCT Filed: Jan. 17, 2012

(86) PCT No.: PCT/US2012/021465
§ 371 (c)(1),
(2), (4) Date: Oct. 1, 2013

(87) PCT Pub. No.: WO2012/099832
PCT Pub. Date: Jul. 26, 2012

(65) Prior Publication Data
US 2014/0378315 A1    Dec. 25, 2014

Related U.S. Application Data

(60) Provisional application No. 61/433,502, filed on Jan. 17, 2011, provisional application No. 61/433,488, filed on Jan. 17, 2011, provisional application No. 61/474,205, filed on Apr. 11, 2011, provisional application No. 61/474,168, filed on Apr. 11, 2011.

(51) Int. Cl.

| | | |
|---|---|---|
| *C12Q 1/68* | (2006.01) | |
| *C12Q 1/6869* | (2018.01) | |
| *C07H 21/00* | (2006.01) | |
| *C12Q 1/6874* | (2018.01) | |
| *A61J 1/14* | (2006.01) | |
| *B65D 8/00* | (2006.01) | |
| *B65B 3/00* | (2006.01) | |
| *B65B 31/04* | (2006.01) | |
| *A61J 1/06* | (2006.01) | |
| *C12N 9/00* | (2006.01) | |
| *C12Q 1/6876* | (2018.01) | |
| *A61M 5/00* | (2006.01) | |
| *B65B 55/08* | (2006.01) | |
| *B65B 55/10* | (2006.01) | |
| *A61M 5/50* | (2006.01) | |

(52) U.S. Cl.
CPC ............ *C12Q 1/6874* (2013.01); *A61J 1/062* (2013.01); *A61J 1/14* (2013.01); *B65B 3/003* (2013.01); *B65B 3/006* (2013.01); *B65B 31/046* (2013.01); *B65D 15/02* (2013.01); *C12N 9/93* (2013.01); *C12Q 1/6876* (2013.01); *A61J 2200/76* (2013.01); *A61J 2205/30* (2013.01); *A61M 5/008* (2013.01); *A61M 5/5086* (2013.01); *B65B 55/08* (2013.01); *B65B 55/10* (2013.01); *C12Q 2600/16* (2013.01); *C12Y 605/01001* (2013.01)

(58) Field of Classification Search
CPC .......... C12Q 1/68; C12Q 1/6869; C07H 21/00
See application file for complete search history.

(56) References Cited

U.S. PATENT DOCUMENTS

| | | |
|---|---|---|
| 4,883,750 A | 11/1989 | Whiteley et al. |
| 4,988,617 A | 1/1991 | Landegren et al. |
| 5,426,180 A | 6/1995 | Kool |
| 5,476,930 A | 12/1995 | Letsinger et al. |
| 5,593,826 A | 1/1997 | Fung et al. |
| 5,871,921 A | 2/1999 | Landegren et al. |
| 5,925,517 A * | 7/1999 | Tyagi .................. C12Q 1/6816 435/6.1 |
| 6,037,130 A * | 3/2000 | Tyagi .................. C12Q 1/6818 435/6.1 |
| 6,872,521 B1 * | 3/2005 | Boyce-Jacino ...... C12Q 1/6827 435/15 |
| 6,949,370 B1 | 9/2005 | Barany et al. |
| 7,255,994 B2 | 8/2007 | Lao |
| 9,315,861 B2 | 4/2016 | Hendricks et al. |
| 9,765,388 B2 | 9/2017 | Hendricks et al. |
| 10,093,969 B2 | 10/2018 | Hendricks et al. |
| 2002/0064779 A1 | 5/2002 | Landegren et al. |
| 2002/0119464 A1* | 8/2002 | McMillan ............. C07K 14/78 435/6.13 |
| 2004/0110213 A1 | 6/2004 | Namsaraev |
| 2008/0003571 A1 | 1/2008 | McKernan et al. |
| 2008/0032310 A1 | 2/2008 | Shannon et al. |
| 2008/0293051 A1 | 11/2008 | Levy et al. |
| 2009/0162840 A1 | 6/2009 | Fredriksson et al. |
| 2010/0081140 A1 | 4/2010 | Church et al. |
| 2011/0008788 A1 | 1/2011 | Paul et al. |
| 2011/0104785 A1 | 5/2011 | Vaidyanathan et al. |

(Continued)

FOREIGN PATENT DOCUMENTS

| | | |
|---|---|---|
| EP | 2665815 | 11/2013 |
| WO | WO-9731256 | 8/1997 |

(Continued)

OTHER PUBLICATIONS

The Stratagene Catalog p. 39 (1988).*
McKernan et al.,Sequence and structural variation in a human genome uncovered by short-read, massively parallel ligation sequencing using two-base encoding. Genome Research 19:1527 (2009).*
Voelkerding et al., Next-Generation Sequencing: From Basic Research to Diagnostics. Clinical Chemistry 55(4) :641 (2009).*
Piserchio et al., Sequence-specific 1H, N, 13C, and 15N backbone resonance assignments of the 34 kDa Paramecium bursaria Chlorella virus 1 (PBCV1) DNA ligase. Biomolecular NMR Assigments 3 (1): 77-80 (2009).*
Skobeltsyna et al., Short Oligonucleotide Tandem Ligation Assay for Genotyping of Single-Nucleotide Polymorphisms in Y Chromosome. Molecular Biotechnology 45 :1-8 (2010).*

(Continued)

*Primary Examiner* — Ethan C Whisenant

(57) ABSTRACT

Methods, assays, compositions and kits for the ligation of short polynucleotides are presented herein. The short polynucleotides are optionally no more than 7 nucleotides in length, and can be as short as 3 or 4 nucleotides in length. The ligation is optionally performed by CV ligase.

22 Claims, 5 Drawing Sheets
Specification includes a Sequence Listing.

(56) References Cited

U.S. PATENT DOCUMENTS

| | | |
|---|---|---|
| 2012/0196294 A1 | 8/2012 | Chen et al. |
| 2019/0024159 A1 | 1/2019 | Hendricks et al. |

FOREIGN PATENT DOCUMENTS

| | | | |
|---|---|---|---|
| WO | WO-2001/061037 | | 8/2001 |
| WO | WO-0192579 | | 12/2001 |
| WO | WO-2004/094456 | | 11/2004 |
| WO | WO-2005/123963 | | 12/2005 |
| WO | 2006/138527 A2 | | 12/2006 |
| WO | WO-2007/107743 | | 9/2007 |
| WO | 2007/121489 | | 10/2007 |
| WO | WO-2007121489 | | 10/2007 |
| WO | WO-2008/016644 | | 2/2008 |
| WO | WO-2009149915 A1 | | 12/2009 |
| WO | WO 2010/151842 | * | 12/2010 |
| WO | WO-2012/099832 | | 7/2012 |
| WO | WO-2012/099896 | | 7/2012 |

OTHER PUBLICATIONS

Wiedmann et al. PCR Methods and Applications 3:S51 (Year: 1994).*
Sriskanda et al, Specificity and fidelity of strand joining by Ch/ore/la virus DNA ligase. Nucleic Acids Research 26 (15) :3536 (Year: 1998).*
Zhang et al., A LDR-PCR Approach for Multiplex Polymorphisms Genotyping of Severely Degraded DNA with Fragment Sizes <100 bp. J. of Forensic Sciences 54 (6) :1304 (Year: 2009).*
"PCT/US2012/021465", International Search Report and Written Opinion mailed, Aug. 27, 2012.
"PCT/US2012/021465", International Preliminary Report on Patentability mailed, Jul. 17, 2013, 11 pages.
Barany, et al., "Genetic Disease Detection and DNA Amplification Using Cloned Thermostable Ligase", Proceedings of the National Academy of Sciences, vol. 88, Issue 1, 1991, 189-193.
Bi, W et al., "CCR: a rapid and simple approach for mutation detection", Nucl. Acids Res., vol. 25(14). 1997, pp. 2949-2951.
Engler, M. J. et al., The Enzymes, 15, 1982, 3-29.
Grossman, et al., "High-Density Multiplex Detection of Nucleic Acid Sequences: Oligonucleotide Ligation Assay and Sequence-Coded Separation", Nucleic Acids Research: vol. 22(21), 1994, 4527-4534.
Higgins, N. Patrick et al., "DNA-Joining Enzymes: A Review", Methods in Enzymology, vol. 68, 1979, 50-71.
Ho, C. Kiong et al., "Characterization of an ATP-Dependent DNA Ligase Encoded by Chlorella Virus PBCV-1", Journal of Virology, vol. 71, No. 3, 1997, 1931-1937.
Landegren, et al., "A Ligase-Mediated Gene Detection Techniaue", Science 241, vol. 241, 1988, 1077-1080.
Landegren, U., Bioessays, 15(11), 1993, 761-765.
Nakajima, Naoki et al., "Mechanism of Amide Formation by Carbodiimide for Bioconjugation in Aqueous Media", Bioconjugate Chemistry, vol. 6, 1995, 123-130.
Nakatani, et al., "Substrate recognition and fidelity of strand joining by an archaeal DNA ligase", Eur. J. Biochem., vol. 269, No. 2, 2002, 650-656.
Odell, Mark et al., "Analysis of the DNA joining repertoire of Chlorella virus DNA ligase and a new crystal structure of the ligase-adenylate intermediate", Nucl. Acids Res., 31(17), 2003, 5090-5100.
Pritchard, Clare et al., "Effects of base mismatches on joining of short oligodeoxynucleotides by DNA ligases", Nucleic Acids Research, Oxford University Press, Surrey, GB, vol. 25, No. 17, 1997, 3403-3407.
Skobeltsyna, Larisa et al., "Short Oligonucleotide Tandem Ligation Assay for Genotyping of Single-Nucleotide Polymorphisms in Y Chromosome", Molecular Biotechnology, vol. 45, No. 1, 2010, 1-8.
Xu, Y et al., "High sequence fidelity in a non-enzymatic DNA autoligation reation", Nucl. Acids. Res., vol. 27(3). 1999, pp. 875-881.
Zirvi, M et al., "Ligase-Based Detection ofMononucleotide Repeat Sequences", Nuc Acids. Res.vol. 27(24), 1999, pp. e40i-e40viii.
Cheng, et al., "Characterization of an ATP-dependent DNA ligase encoded by Haemophilus influenzae", Nucleic Acids Research, vol. 25, No. 7, Jan. 1, 1997, 1369-1374.
Fredriksson, et al., "Protein detection using proximity-dependent DNA ligation assays", Nature Biotechnology vol. 20, May 1, 2002, 473-477.
Gullberg, et al., "Cytokine Detection by Antibody-based Proximity Ligation", Proceedings of National Academy of Science, vol. 101, No. 22, Jun. 1, 2004, 8420-8424.
Holland, et al., "Detection of Specific Polymerase Chain Reaction Product by Utilizing the 5'>3' Exonuclease Activity of Thermus Aquaticus DNA Polymerase", Proceedings of the National Academy of Sciences, vol. 88, Issue 16, Aug. 15, 1991, 7276-7280.
Horspool, et al., "Efficient assembly of very short oligonucleotides using T4 DNA ligase", BMC Research Notes 201, vol. 3, No. 291, 2010, 1-9.
Intl PCT/US2012/021585, "International Preliminary Report on Patentability", dated Jul. 17, 2013, 1-11.
Intl PCT/US2012/021585, "International Search Report and Written Opinion", dated Jul. 6, 2012, 1-18.
Kim, et al., "Improvement of Sensitivity and Dynamic Range in Proximity Ligation Assays by Symmetric Connector Hibridization", Analytical Chemistry, vol. 82, No. 16, Aug. 15, 2010, 6976-6982.
Piserchio, et al., "Sequence-specific 1H N, 13C, and 15N backbone resonance assignments of the 34 kDa Paramecium bursaria Chlorella virus 1 (PBCV1) DNA liagase", Biomolecular NMR Assignments, vol. 3, No. 1, Jun. 2009, 77-80.
Piserchio, et al., "Solution NMR Studies of Chlorella Virus DNA Ligase-adenylate", Journal of Molecular Biology vol. 395, No. 2, Jan. 15, 2010, 291-308.
Swartzman, et al., "Expanding applications of protein analysis using proximity ligation and aPCR", Methods: A Companion to Methods in Enzymology, vol. 5, No. 4, Apr. 1, 2010, S23-S26.
Lohman et al., (2014) Efficient DNA ligation in DNA-RNA hybrid helices by Chlorella virus DNA ligase. Nucleic Acids Research, 2014, vol. 42, 1831-1844.
Sriskanda, V. and Shuman, S. (1998) Specificity and fidelity of strand joining by Chlorella virus DNA ligase. Nucleic Acids Res., 26, 3536-3541.
EP1716644.4, EP Extended Search Report dated May 30, 2017, 1-14 pp.
EP17185075.3, Extended European Search Report dated Nov. 14, 2017, 1-10.
Gustafsdottir, Sigrun M, et al., "Proximity ligation assays for sensitive and specific protein analyses", Analytical Biochemistry, 2005, 2-9.
Ahei, et al. (The neurodegenerative disease protein aprataxin resolves abortive DNA ligation intermediates, Nature. Oct. 12, 2006;443(7112):713-6. Epub Sep. 10, 2006).
Odell and Shuman (Footprinting of Chlorelia Virus DNA Ligase Bound at a Nick in Duplex DNA, The Journal of Biological Chemistry 274, 14032-14039, May 14, 1999).
Rass, Ulrich et al., "Actions of Aprataxin in Multiple DNA Repair Pathways", Journal of Biological Chemistry, vol. 282, No. 13, 2007, 9469-9474.
Rass, Ulrich et al.. "Molecular Mechanism of DNA Deadanylation by the Neurological Disease Protein Aprataxin", Journal of Biological Chemistry, vol. 283, No. 49, 2008, 33994-34001.

* cited by examiner

FIGURE 1
(A)
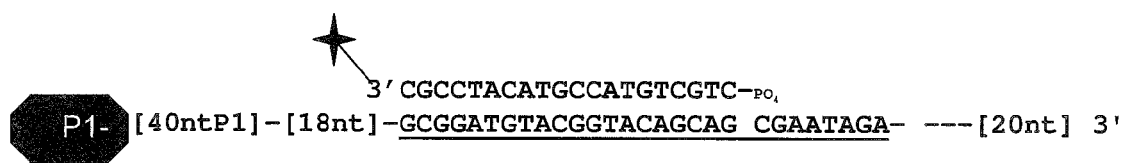
3' CGCCTACATGCCATGTCGTC-PO₄
P1- [40ntP1]-[18nt]-GCGGATGTACGGTACAGCAG CGAATAGA- ---[20nt] 3'
(B)
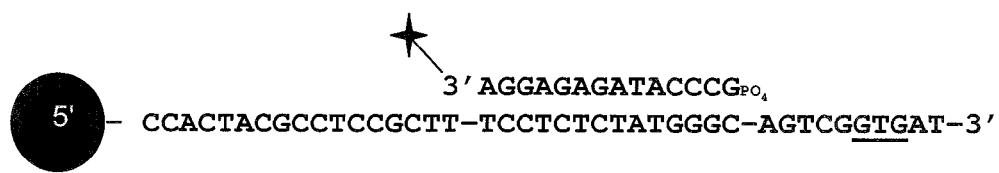
3' AGGAGAGATACCCG-PO₄
5' - CCACTACGCCTCCGCTT-TCCTCTCTATGGGC-AGTCGGTGAT-3'

FIGURE 2

CV DNA Ligase, GenBank ID AAC96909.1, from Paramecium bursaria Chlorella virus 1:

MAITKPLLAATLENIEDVQFPCLATPKIDGIRSVKQTQMLSRTFKPIRNSVMNRLLTELL
PEGSDGEISIEGATFQDTTSAVMTGHKMYNAKFSYYWFDYVTDDPLKKYIDRVEDMK
NYITVHPHILEHAQVKIIPLIPVEINNITELLQYERDVLSKGFEGVMIRKPDGKYKFGRST
LKEGILLKMKQFKDAEATIISMTALFKNTNTKTKDNFGYSKRSTHKSGKVEEDVMGSIE
VDYDGVVFSIGTGFDADQRRDFWQNKESYIGKMVKFKYFEMGSKDCPRFPVFIGIRHE
EDR

MnM DNA Ligase, GenBank ID YP_333052.1, from Burkholderia pseudomallei 1710b (equivalent sequence to ABA50091)

MSGVPYGFKPNLAATLTKPELIKFPVWASPKIDGIRCVFFGGVAYSRSLKPIPNPVVQEF
AKAYANLLEGLDGELTVGSPTDANCMQNSMAVMSKAAAPDFTFHVFDWFHPAQAHI
EFWQRSDVVEDRIVQFYDRYPEVDIRAAPQVLCTSLAHLDTNEARWLADGYEGMMIR
DHCGRYKFGRSTEREGGLVKVKRFTDAEAIVIGFEEEMHNANEAKRDATGRTERSTSK
AGLHGKGTLGALVVKNERGIVFNIGTGFTAAQRADYWANHPSLFGKMVKFKHFDHGT
VDAPRHPVFIGFRHPEDM

Hin DNA Ligase, GenBank ID P44121, from Haemophilus influenza

MKFYRTLLLFFASSFAFANSDLMLLHTYNNQPIEGWVMSEKLDGVRGYWNGKQLLTR
QGQRLSPPAYFIKDFPPFAIDGELFSERNHFEEIS T ITKSFKGDGWEKLKLYVFDVPDAE
GNLFERLAKLKAHLLEHPTTYIEIIEQIPVKDKTHLYQFLAQVENLQGEGVVVRNPNAP
YERKRSSQILKLKTAR G EECTVIAHHKGKGQFENVMGALTCKNHRGEFKIGSGFNLNE
RENPPPIGSVITYKYRGITNSGKPRFATYWREKK

DLX DNA Ligase, artificial ligase derived from Hin DNA ligase from Haemophilus influenza:

MKFYRTLLLFFASSFAFANSDLMLLHTYNNQPIEGWVMSEKLDGVRGYWNGKQLLTR
QGQRLSPPAYFIKDFPPFAIDGELFSERNHFEEIS S ITKSFKGDGWEKLKLYVFDVPDAEG
NLFERLAKLKAHLLEHPTTYIEIIEQIPVKDKTHLYQFLAQVENLQGEGVVVRNPNAPY
ERKRSSQILKLKTARGEECTVIAHHKGKGQFENVMGALTCKNHRGEFKIGSGFNLNER
ENPPPIGSVITYKYRGITNSGKPRFATYWREKK

DLXd DNA Ligase, artificial ligase derived from Hin D ligase from Haemophilus influenza:

MKFYRTLLLFFASSFAFANSDLMLLHTYNNQPIEGWVMSEKLDGVRGYWNGKQLLTR
QGQRLSPPAYFIKDFPPFAIDGELFSERNHFEEIS S ITKSFKGDGWEKLKLYVFDVPDAEG
NLFERLAKLKAHLLEHPTTYIEIIEQIPVKDKTHLYQFLAQVENLQGEGVVVRNPNAPY
ERKRSSQILKLKTAR D EECTVIAHHKGKGQFENVMGALTCKNHRGEFKIGSGFNLNER
ENPPPIGSVITYKYRGITNSGKPRFATYWREKK

DLXd2 DNA Ligase (Gammaproteobacteria, Haemophilus influenza) (modified)

MLLHTYNNQPIEGWVMSEKLDGVRGYWNGKQLLTRQGQRLSPPAYFIKDFPPFAIDGE
LFSERNHFEEIS S ITKSFKGDGWEKLKLYVFDVPDAEGNLFERLAKLKAHLLEHPTTYIE
IIEQIPVKDKTHLYQFLAQVENLQGEGVVVRNPNAPYERKRSSQILKLKTAR D EECTVIA
HHKGKGQFENVMGALTCKNHRGEFKIGSGFNLNERENPPPIGSVITYKYRGITNSGKPR
FATYWREKK

FIGURE 3
(A)
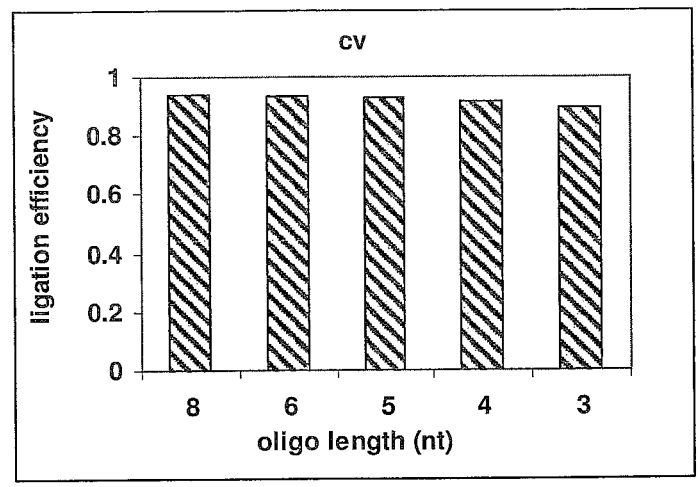
(B)
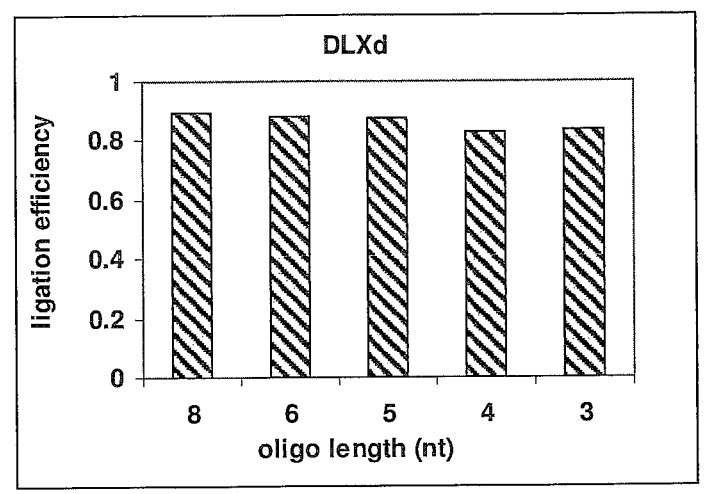
(C)
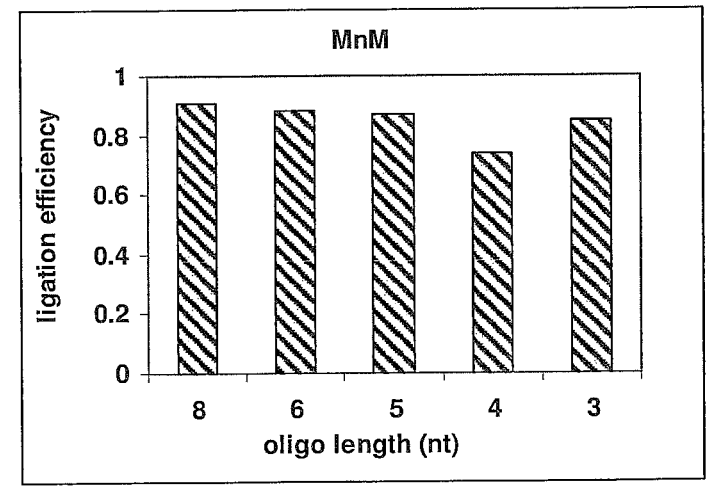

FIGURE 4
(A)
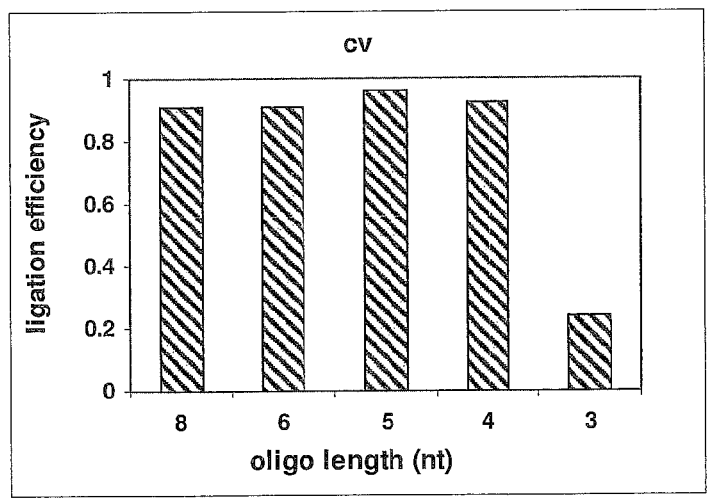
(B)
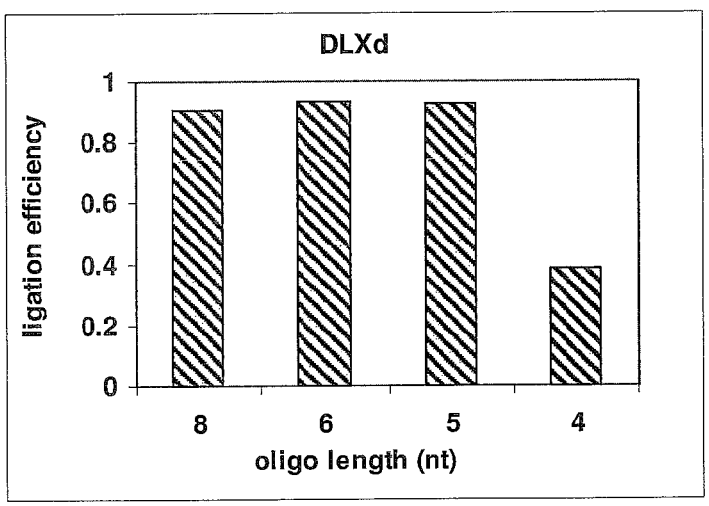
(C)
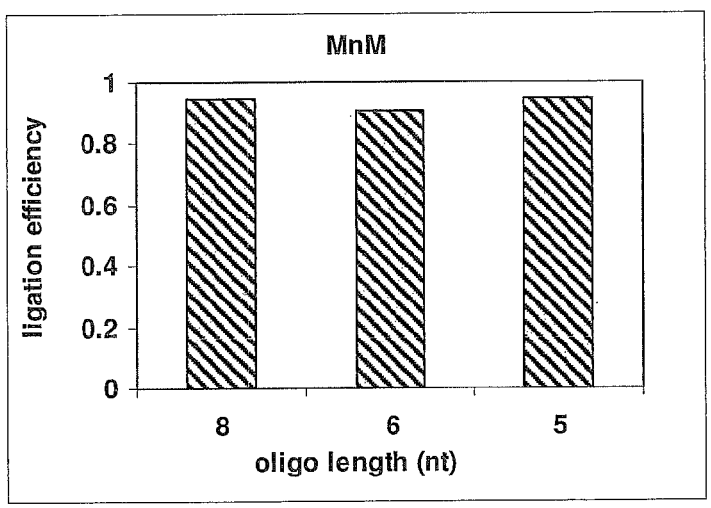

ENZYMATIC LIGATION OF NUCLEIC ACIDS

This application is a U.S. National Application filed under 35 U.S.C. §371 of International Application No. PCT/US2012/021465, filed Jan. 17, 2012 which claims priority to U.S. Ser. No. 61/433,502 filed Jan. 17, 2011 and U.S. Ser. No. 61/433,488 filed Jan. 17, 2011, U.S. Ser. No. 61/474,205 filed Apr. 11, 2011, and U.S. Ser. No. 61/474,168 filed Apr. 11, 2011, the disclosures of which are hereby incorporated by reference in their entirety as if set forth fully herein.

BACKGROUND

DNA ligases can join polynucleotides together, for example by catalyzing the formation of a phosphodiester bond at single- or double-stranded breaks on duplex DNA. Ligases can be sensitive to the degree of hybridization between opposing nucleic acid strands in a duplex. For example, successful ligation can occur less frequently (or not at all) where a strand to be ligated to an adjacent strand is in a duplex and is not complementary to its opposing strand in the duplex. In some cases a single nucleotide mismatch between strands in a duplex can significantly impair or prevent ligation. The capacity of ligases for discrimination based on hybridization, including single nucleotide discrimination, has led to the development of ligase-mediated detection techniques (e.g., Landegren, U., Bioessays, 15(11):761-765 (1993), and Barany, PNAS USA, 88(1):189-193 (1991)). Ligase-based linear signal amplification known as LDR (i.e., ligase detection reaction), combined with PCR (i.e., polymerase chain reaction)-based gene specific target amplification, has been proven to be a useful tool in cancer and disease gene mutation detection. PCR/LDR techniques typically rely on two properties of a DNA ligase: (i) specificity, and (ii) thermostability.

SUMMARY

This application relates to ligation reagents and methods. Among other things, methods of and reagents for ligating nucleic acids to other nucleic acids are provided, including ligation of two polynucleotides. Either or both polynucleotides can be single-stranded or double-stranded. One or both polynucleotides can be a short oligonucleotide. In some embodiments oligonucleotides and/or polynucleotides of different lengths can be ligated to each other. The ligation can be enzymatic, and ligations can be template-dependent or template-independent. The nucleic acids that are ligated or involved in the ligation reaction can be labeled or unlabeled and immobilized or in solution.

Some embodiments involve template-independent ligation of double-stranded or single-stranded polynucleotides (e.g., oligonucleotides). The single-stranded polynucleotides are optionally not hybridized to another polynucleotide. In some embodiments, an oligonucleotide can be hybridized to or otherwise associated with all or a portion of an overhang or other single-stranded region of a duplex nucleic acid and ligated to a free end of a strand of the duplex or to another oligonucleotide that is hybridized or otherwise associated with an overhang or other single-stranded portion of the duplex.

Some embodiments involve ligation of single-stranded polynucleotides (e.g., oligonucleotides). Optionally, the single-stranded polynucleotides are hybridized hybridized adjacent or near each other on another single polynucleotide. In some embodiments, an oligonucleotide can be hybridized to or otherwise associated with all or a portion of an overhang or other single-stranded region of a duplex nucleic acid and ligated to a free end of a strand of the duplex or to another oligonucleotide that is hybridized or otherwise associated with an overhang or other single-stranded portion of the duplex.

In some aspects, methods and reagents are provided for hybridizing or otherwise associating a first oligonucleotide and a second oligonucleotide to a third oligonucleotide or to a polynucleotide such that the termini of the first and second oligonucleotides are adjacent to or near each other. Such hybridization or association can occur sequentially, simultaneously, or substantially simultaneously. The terminus of the first oligonucleotide can be ligated to the adjacent or nearby terminus of the second oligonucleotide.

Nucleotide base mismatches between a first and/or second oligonucleotide and a third oligonucleotide or polynucleotide can affect the efficiency of ligation. For example, mismatches at the terminal position of either or both a first and second oligonucleotides can affect ligation efficiency, reducing the probability of successful ligation or precluded ligation entirely. Mismatches at other or at multiple positions can also affect ligation efficiency, reducing the probability of successful ligation or precluding ligation entirely.

Also provided are methods and reagents for performing multiple ligations sequentially, in parallel, or both sequentially and in parallel.

Optionally, one or more of the primer, probe or template is labeled. For example the probe can be labeled. Else the primer or template is labeled.

In some embodiments, methods of ligation are provided that provide information about the sequence of a nucleic acid. For example, in some aspects a ligation can be performed in the presence of multiple oligonucleotides that are at least partially complementary to a target region on a template. Oligonucleotide probes can be used that hybridize or otherwise associate with a template adjacent to or near a terminus of a primer or probe that is hybridized to or otherwise associated with a template. Multiple oligonucleotide probes, each at least partially complementary to a region of a template can be used to determine sequence information in a template-dependent manner as is known in the art. For example, oligonucleotide ligation is used to determine nucleic acid sequence information in the SOLiD System (Life Technologies-Applied Biosystems, Carlsbad, Calif.). According to some embodiments, sequence information is determined ligating oligonucleotide probes to an oligonucleotide primer in a template sequence-dependent manner, for example by using a SFL. The oligonucleotide probes can be a set of multiple probes having different sequences and distinguishing labels, and the primer and probes can have lengths of not more than 8, 7, 6, 5, 4, 3 or 2 nucleotides. The labels can provide information about the sequence of the probe.

In some embodiments, ligation can be performed by a "small footprint ligase" (herein "SFL") that can ligate short polynucleotides. SFLs can be used in each of the embodiments of ligations discussed above and in the remainder of this disclosure, as well as in other embodiments of ligations known to person of skill in the art. For example, in some embodiments an SFL can ligate the termini of a first oligonucleotide and a second oligonucleotide. The first oligonucleotide can be a primer and the second oligonucleotide can be a probe, each hybridizing or otherwise associating with a portion of a third oligonucleotide or a polynucleotide.

In some embodiments, the SFL can ligate oligonucleotides that are 8, 7, 6, 5, 4, 3 or 2 nucleotides in length to a polynucleotide. Ligation of such oligonucleotides can be to oligonucleotides of the same length or of different length or to a polynucleotide. For example, an oligonucleotide of 2 or 3 nucleotides in length can be ligated to an oligonucleotide of 2, 3, 4, 5, 6, 7, 8 or more nucleotides in length or to longer oligonucleotides or to a polynucleotide.

Also provided are kit comprising a small footprint ligase ("SFL") or functional variant or fragment or derivative thereof. Exemplary SFLs are identified herein, and their sequences provided. Optionally, the kit can also include one or more oligonucleotide probes less than 12 nucleotides in length, (e.g., not more than 8, 6, 5, 4, 3 or 2 nucleotides in length). Optionally, the kit includes CV ligase and one or more oligonucleotides probes less than 6 nucleotides in length.

BRIEF DESCRIPTION OF THE DRAWINGS

FIG. 1. (A) Extended P1 covalent bead ligation substrate. Shown is a ligation substrate designed to mimic the conditions used in SOLiD™ sequencing. FIG. 1(A) represents DNA covalently linked to a bead (such as a magnetic bead, e.g., of 0.1 to 1 µm diameter). DNA on this bead was enriched by PCR using the 40 nucleotide P1 sequence. To the region GCGGATGTACGGTACAGCAG, a 20-mer complementary "primer" is annealed that has a 5' $PO_4$ which reacts with the 3'OH group of the SOLiD probe, as well as a 3' fluorescent label for detection using capillary electrophoresis. To the overhang sequence CGAATAGA, complementary probes can hybridize to demonstrate the ligation reaction. (B) P1 covalent bead ligation substrate. Shown is a similar ligation substrate to that in FIG. 1(A), however the reaction in this case will occur much closer to the bead surface. Probes are hybridized to the overhang region AGTCGGTGAT, where the underlined residues are opposite the inosine triplet of probes having the structure Dye-5' III (s)-xy-NNN 3', as described in further detail herein.

FIG. 2: Sequences of exemplary ligases. The GenBank ID and source organism are provided where applicable. Three artificial ligases are also provided. DLX differs from Hin DNA Ligase at 1 amino acid—designated as the underlined emboldened letter. DLXd differs from Hin DNA Ligase at 2 amino acids—designated as the underlined emboldened letters. DLXd2 is 22 amino acids shorter than Hin DNA Ligase and differs from Hin DNA Ligase at 2 amino acids, designated as the underlined emboldened letters.

FIG. 3: Ligation of short oligonucleotides with various ligases. Ligation of short oligonucleotides with (A) CV ligase, (B) DLXd ligase and (C) MnM ligase. Forward ligation reactions were performed under the following conditions: 2.0 µM ligase, 2-5 µM short oligo, 2.0 nM primer/template (tethered to magnetic beads) and proceeded for 20 minutes at 15° C. The ligation efficiency was calculated as the as the ratio of peak areas determined by CE where a FAM labeled primer was used. Efficiency=ligated/(ligated+unligated).

FIG. 4: Ligation of short oligonucleotides with various ligases. Ligation of short oligonucleotides with (A) CV ligase, (B) DLXd ligase and (C) MnM ligase. Reverse ligation reactions were performed under the following conditions: 2.0 µM ligase, 2-5 µM short oligo, 2.0 nM primer/template (tethered to magnetic beads) and proceeded for 20 minutes at 15° C. The ligation efficiency was calculated as the as the ratio of peak areas determined by CE where a FAM labeled primer was used. Efficiency=ligated/(ligated+unligated).

DEFINITIONS

Figure 5:
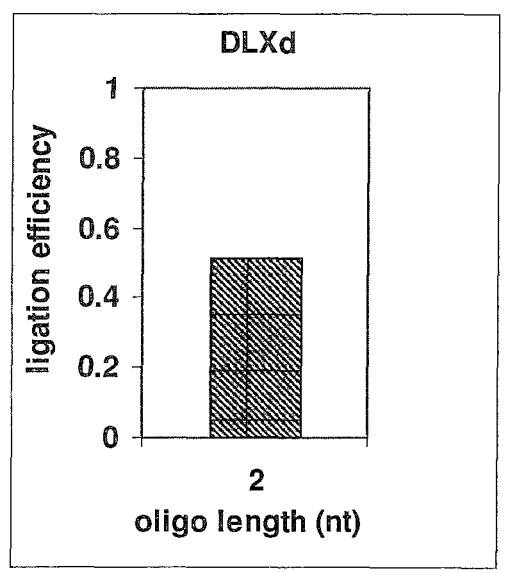
FIG. 5: Ligation of 2-mers. Ligation reaction in the forward direction was performed under the following conditions: 2.0 µM DLXd, 123 µM dinucleotide (5'-CG-3'), 2.0 nM primer/template (tethered to magnetic beads) and proceeded for 20 minutes at 15° C. The ligation efficiency was calculated as the as the ratio of peak areas determined by CE where a FAM labeled primer was used. Efficiency=ligated/(ligated+unligated).

"Degenerate", with respect to a position in a polynucleotide that is one of a population of polynucleotides, means that the identity of the base of the nucleoside occupying that position varies among different members of the population. A population of polynucleotides in this context is optionally a mixture of polynucleotides within a single continuous phase (e.g., a fluid). The "position" can be designated by a numerical value assigned to one or more nucleotides in a polynucleotide, generally with respect to the 5' or 3' end. For example, the terminal nucleotide at the 3' end of an extension probe may be assigned position 1. Thus in a pool of extension probes of structure 3'-XXXNXXXX-5', the N is at position 4. A position is said to be k-fold degenerate if it can be occupied by nucleosides having any of k different identities. For example, a position that can be occupied by nucleosides comprising either of 4 different bases is 4-fold degenerate.

Along similar lines, it should be understood that a statement that a result has occurred (e.g., ligation, binding) is intended to indicate that the result has occurred at a significant or substantial level or an enhanced level compared to when it has not occurred. For example. Ligation is said to have not occurred if it is not significant, insubstantial or greatly reduced (e.g., reduced by at least 80%, 90%, 95% or 99% compared to when ligation does occur (e.g., under the conditions described in the last paragraph).

The terms "microparticle," "beads" "microbeads", etc., refer to particles (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymethymethacrylate, titanium dioxide, latex, polystyrene, etc. Magnetization can facilitate collection and concentration of the microparticle-attached reagents (e.g., polynucleotides or ligases) after amplification, and facilitates additional steps (e.g., washes, reagent removal, etc.). In certain embodiments of the invention a population of microparticles having different shapes sizes and/or colors can be used. The microparticles can optionally be encoded, e.g., with quantum dots such that each microparticle can be individually or uniquely identified.

The term "sequence" refers to sequence information about a polynucleotide or polypeptide or any portion of the polynucleotide or polypeptide that is two or more units (nucleotides or amino acids) long. The term can also be used as a reference to the polynucleotide or polypeptide molecule itself or a relevant portion thereof. Polynucleotide sequence information relates to the succession of nucleotide bases on the polynucleotide, and in a polypeptide relates to the succession of amino acid side chains in the polypeptide or portion thereof. For example, if the polynucleotide contains bases Adenine, Guanine, Cytosine, Thymine, or Uracil, the polynucleotide sequence can be represented by a corresponding succession of letters A, G, C, T, or U), e.g., a DNA or RNA molecule. Sequences shown herein are presented in a 5'→3' orientation unless otherwise indicated.

"Perfectly matched duplex" in reference to probes and template polynucleotides means that one forms a double stranded structure with the other such that each nucleoside in the double stranded structure undergoes Watson-Crick basepairing with a nucleoside on the other. The term also comprehends the pairing of nucleoside analogs, such as deoxyinosine, nucleosides with 2-aminopurine bases, and the like, that may be employed to reduce the degeneracy of the probes, whether or not such pairing involves formation of hydrogen bonds.

The term "polymorphism" is given its ordinary meaning in the art and refers to a difference in genome sequence among individuals of the same species. A "single nucleotide polymorphism" (SNP) refers to a polymorphism at a single position.

"Probes", "oligonucleotides" or "primers" are intended to be interchangeable terms herein, so that any one of these can be taken as a reference to another. These are polynucleotides not necessarily limited to any length. Where so wished, these can be less than 100 nucleotides long, sometimes less than 30 nucleotides long, e.g., less than 20 nucleotides, optionally less than 12 nucleotides, for example less than eight nucleotides in length. In some cases, these are 2, 3, 4, 5, 6, 7, 8, or more nucleotides in length. In some cases, these are 3 or 4 nucleotides in length.

A "polynucleotide," also called a "nucleic acid," is a linear polymer of two or more nucleotides joined by covalent internucleosidic linkages, or variant or functional fragment thereof. A sequence of letters, such as "ATGCCTG," is intended to represent a polynucleotide sequence in the 5'→3' order from left to right unless otherwise specified. In naturally occuring examples of these, the internucleoside linkage is typically a phosphodiester bond. However, other examples optionally comprise other internucleoside linkages, such as phosphorothiolate linkages and may or may not comprise a phosphate group. In other cases, the polynucleotide can contain non-nucleotidic backbones, for example, polyamide (e.g., peptide nucleic acids (PNAs)) and polymorpholino and other synthetic sequence-specific nucleic acid polymers providing that the polymers contain nucleobases in a configuration which allows for base pairing and base stacking, such as is found in DNA and RNA.

As used herein, "polynucleotide," "oligonucleotide", "probe", "primer", "template", "nucleic acid" and the like can be taken to refer to a populations or pools of individual molecules that are substantially identical across their entire length or across a relevant portion of interest. For example, the term "template" can indicate a plurality of template molecules that are substantially identical, etc. In the case of polynucleotides that are degenerate at one or more positions, it will be appreciated that the degenerate polynucleotide comprises a plurality of polynucleotide molecules, which have sequences that are substantially identical only at the nondegenerate position(s) and differ in sequence at the degenerate positions. Thus, reference to "a" polynucleotide (e.g., "a" primer, probe, oligonucleotide, template, etc.) can be taken to mean a population of polynucleotide molecules that are substantially identical over at least a portion of interest, such that the plural nature of the population need not be explicitly indicated, but can if so desired. These terms are also intended to provide adequate support for a claim that explicitly specifies a single polynucleotide molecule itself. It will be understood that members of a population need not be 100% identical, e.g., a certain number of "errors" may occur during the course of synthesis. Preferably at least 90%, at least 95%, at least 99%, or more of the members of a population are substantially identical. Preferably the percent identity of at least 95% or more preferably at least 99% of the members of the population to a reference nucleic acid molecule is at least 98%, 99%, 99.9% or greater. Percent identity may be computed by comparing two optimally aligned sequences, determining the number of positions at which the identical nucleic acid base (e.g., A, T, C, G, U, or I) occurs in both sequences to yield the number of matched positions, dividing the number of matched positions by the total number of positions, and multiplying the result by 100 to yield the percentage of sequence identity. It will be appreciated that in certain instances a nucleic acid molecule such as a template, probe, primer, etc., may be a portion of a larger nucleic acid molecule that also contains a portion that does not serve a template, probe, or primer function. In that case individual members of a population need not be substantially identical with respect to that portion.

The nucleotides of a polynucleotide can have any combination of bases, including those mentioned herein, for example uracil, adenine, thymine, cytosine, guanine, inosine, xathanine hypoxathanine, isocytosine, isoguanine, etc. Optionally, the polynucleotide is a DNA having the nucleotide bases A, C, T and/or G. Optionally, the polynucleotide is an RNA having the nucleotide bases A, C, T and/or U.

Polynucleotides include double- and single-stranded DNA, as well as double- and single-stranded RNA, DNA: RNA hybrids, peptide-nucleic acids (PNAs) and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. Polynucleotides can optionally be attached to one or more non-nucleotide moieties such as labels and other small molecules, large molecules such proteins, lipids, sugars, and solid or semi-solid supports, for example through either the 5' or 3' end. Labels include any moiety that is detectable using a detection method of choice, and thus renders the attached nucleotide or polynucleotide similarly detectable using a detection method of choice. Optionally, the label emits electromagnetic radiation that is optically detectable or visible. In some cases, the nucleotide or polynucleotide is not attached to a label, and the presence of the nucleotide or polynucleotide is directly detected, and/or the generation of byproducts of ligation such as PPi or NMN is detected. Optionally, the presence of the nucleotide, polynucleotide or byproduct is sensed by a chemical field-effect transistor, e.g., where the charge on the gate electrode is generated by a chemical process. Optionally, the chemical field-effect transistor is an ion-sensitive field-effect transistor.

Where two or more reagents are labeled, the labels are preferably distinguishable from each other with the detection method of choice. For example, the labels can be spectrally resolvable, i.e., distinguishable on the basis of their spectral characteristics, particularly fluorescence emission wavelength, under conditions of operation. In other instances, the label may comprise a signal-generating compound (SGC). A SGC is optionally a substance that it itself detectable in an assay of choice, or capable of reacting to form a chemical or physical entity (i.e., a reaction product) that is detectable in an assay of choice. Representative examples of reaction products include precipitates, fluorescent signals, compounds having a color, and the like. Representative SGC include e.g., bioluminescent compounds (e.g., luciferase), fluorophores (e.g., below), bioluminescent and chemiluminescent compounds $^{131}$I, $^{125}$I, $^{14}$C, $^{3}$H, $^{35}$S, $^{32}$P, radioisotopes (e.g., P and the like) enzymes (e.g., below), binding proteins (e.g., biotin, avidin, streptavidin and the like), magnetic particles, chemically reactive compounds (e.g., colored stains), labeled oligonucleotides; molecular probes (e.g., CY3, Research Organics, Inc.), and the like. Representative fluorophores include fluorescein isothiocyanate, succinyl fluorescein, rhodamine B, lissamine, 9,10-diphenlyanthracene, perylene, rubrene, pyrene and fluorescent derivatives thereof such as isocyanate, isothiocyanate, acid chloride or sulfonyl chloride, umbelliferone, rare earth chelates of lanthanides such as Europium (Eu) and the like. Signal generating compounds also include SGC whose products are detectable by fluorescent and chemiluminescent wavelengths, e.g., sequencing dyes, luciferase, fluorescence emitting metals such as $^{152}$Eu, or others of the lanthanide series; compounds such as luminol, isoluminol, acridinium salts, and the like; bioluminescent compounds such as luciferin; fluorescent proteins (e.g., GFP or variants thereof); and the like. The subject SGC are optionally detectable using a visual or optical method; preferably, with a method amenable to automation such as a spectrophotometric method, a fluorescence method, a chemiluminescent method, an electrical nanometric method involving e.g., a change in conductance, impedance, resistance and the like and a magnetic field method. Some SGC's are optionally detectable with the naked eye or with a signal detection apparatus when at an appropriate concentration.

A "nucleotide" refers to a nucleotide, nucleosideor analog thereof. Optionally, the nucleotide is an N- or C-glycoside of a purine or pyrimidine base. (e.g., deoxyribonucleoside containing 2-deoxy-D-ribose or ribonucleoside containing D-ribose). Examples of other analogs include, without limitation, phosphorothioates, phosphoramidates, methyl phosphonates, chiral-methyl phosphonates, 2-O-methyl ribonucleotides.

Nucleotide bases or nucleobases usually have a substituted or unsubstituted parent aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-Δ2-isopentenyladenine (6iA), N6-Δ2-isopentenyl-2-methylthioadenine (2ms6iA), N6-methyladenine, guanine (G), isoguanine, N2-dimethylguanine (dmG), 7-methylguanine (7 mG), 2-thiopyrimidine, 6-thioguanine (6sG) hypoxanthine and O6-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, O4-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. In certain embodiments, nucleotide bases are universal nucleotide bases. Additional exemplary nucleotide bases can be found, e.g., in Fasman, 1989, Practical Handbook of Biochemistry and Molecular Biology, pp. 385-394, CRC Press, Boca Raton, Fla., and the references cited therein. A nucleoside is usually a compound having a nucleotide base covalently linked to the C-1' carbon of a pentose sugar. In certain embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, (C1-C6) alkyl or (C5-C14) aryl. The pentose sugar may be saturated or unsaturated. Exemplary pentose sugars and analogs thereof include, but are not limited to, ribose, 2'-deoxyribose, 2'-(C1-C6)alkoxyribose, 2'-(C5-C14)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose. One or more of the pentose carbons of a nucleoside may be substituted with a phosphate ester, as disclosed in U.S. Pat. No. 7,255,994. In certain embodiments, the nucleosides are those in which the nucleotide base is a purine, a 7-deazapurine, a pyrimidine, a universal nucleotide base, a specific nucleotide base, or an analog thereof. Nucleotide analogs include derivatives in which the pentose sugar and/or the nucleotide base and/or one or more of the phosphate esters of a nucleoside may be replaced with its respective analog. Exemplary pentose sugar analogs and nucleotide base analog are described above. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions. Other nucleotide analogs are nucleotide analog monomers which can be polymerized into polynucleotide analogs in which the DNA/RNA phosphate ester and/or sugar phosphate ester backbone is replaced with a different type of linkage. Exemplary polynucleotide analogs include, but are not limited to, peptide nucleic acids, in which the sugar phosphate backbone of the polynucleotide is replaced by a peptide backbone.

The internucleoside linkages can be a phosphodiester linkage, although other linkages (e.g., scissile linkages which can be substantially cleaved under conditions in which phosphodiester linkages are not substantially cleaved) can be used. For example, a linkage that contains an AP endonuclease sensitive site, for example an abasic residue, a residue containing a damaged base that is a substrate for removal by a DNA glycosylase, or another residue or linkage that is a substrate for cleavage by an AP endonuclease, or a disaccharide nucleoside.

The adjectival term "hybridized" optionally refers to two polynucleotides which are bonded to each other by two or more sequentially adjacent base pairings. The term "hybridization" refers to the process by which polynucleotides become hybridized to each other. Two single-stranded polynucleotides can be regarded as "complementary" if when hybridized together the longer polynucleotide forms a single-stranded overhang and the shorter polynucleotide can be efficiently ligated to a third adjacent polynucleotide that forms a perfectly-matched duplex with the single-stranded overhang. Where the single-stranded overhang is less than eight nucleotides, it can be arbitrarily lengthened to eight nucleotides by adding a random combination of nucleotides to the overhang.

Similarly, nucleotide residues can be regarded as complementary if when both are base-paired with each other within two hybridized polynucleotides, either nucleotide can be ligated in a template-driven ligation reaction when situated as the terminal nucleotide in its polynucleotide. Nucleotides that are efficiently incorporated by DNA polymerases opposite each other during DNA replication under physiological conditions are also considered complementary. In an embodiment, complementary nucleotides can form base pairs with each other, such as the A-T/U and G-C base pairs formed through specific Watson-Crick type hydrogen bonding between the nucleobases of nucleotides and/or polynucleotides positions antiparallel to each other. The complementarity of other artificial base pairs can be based on other types of hydrogen bonding and/or hydrophobicity of bases and/or shape complementarity between bases.

In appropriate instances, polynucleotides can be regarded as complementary when they can undergo cumulative base pairing at two or more individual corresponding positions in antiparallel orientation, as in a hybridized duplex. Optionally there can be "complete" or "total" complementarity between a first and second polynucleotide sequence where each nucleotide in the first polynucleotide sequence can undergo a stabilizing base pairing interaction with a nucleotide in the corresponding antiparallel position on the second polynucleotide. "Partial" complementarity describes polynucleotide sequences in which at least 20%, but less than 100%, of the residues of one polynucleotide are complementary to residues in the other polynucleotide. A "mismatch" is present at any position in which the two opposed nucleotides are not complementary. In some ligation assays, a polynucleotide can undergo substantial template-dependent ligation even when it has one or more mismatches to its hybridized template. Optionally, the polynucleotide has no more than 4, 3, or 2 mismatches, e.g., 0 or 1 mismatch, with its template. In some assays, the polynucleotide will not undergo substantial template-dependent ligation unless it is at least 60% complementary, e.g., at least about 70%, 80%, 85%, 90%, 95%, 99% or 100% complementary to its template.

As used herein, a "biological sample" refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

Sequence identity (also called homology) refers to similarity in sequence of two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 90% identity at the amino acid level or at the nucleotide level. Preferably, the identity exists over a region that is at least about 2, 3, 4, 5, 6, 7, 8, 10, 12, 15, 20, 25, 50, or 100 residues in length, or across the entire length of at least one compared sequence. A preferred algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent conditions.

In the claims, any active verb (or its gerund) is intended to indicate the corresponding actual or attempted action, even if no actual action occurs. For example, the verb "hybridize" and gerund form "hybridizing" and the like refer to actual hybridization or to attempted hybridization by contacting nucleic acid sequences under conditions suitable for hybridization, even if no actual hybridization occurs. Similarly, "detecting" and "detection" when used in the claims refer to actual detection or to attempted detection, even if no target is actually detected.

"Nonspecific hybridization" is used to refer to any unintended or insignificant hybridization, for example hybridization to an unintended polynucleotide sequence other than the intended target polynucleotide sequence. The uninentended polynucleotide sequence can be on the same or different polynucleotide from the intended target. In some cases, the only intended hybridization can be from Watson-Crick base pairing between two polynucleotides. Other kinds of intended base pairings can include base pairing between corresponding analogs of such nucleotides or between iso-cytidine and iso-guanine. In some cases where hybridization is only intended between complementary bases, any bonding between non-complementary bases is considered to be non-specific hybridization.

In reference to ligation of two polynucleotides, the "proximal" terminus of either polynucleotide is the terminus that is intended to be ligated to the other polynucleotide. This is generally the terminus that is contacted by the active site of the ligase, or the terminus that is eventually ligated to the other polynucleotide, while the opposite terminus is the "distal" terminus. The terminal nucleotide residue at the proximal terminus can be termed the proximal nucleotide, and the proximal nucleotide position optionally designated as position 1, or −1 depending on which side of the ligation site we are referring to, the penultimate nucleotide position as position 2 or −2, etc. With reference to two adjacently-hybridized polynucleotides, the proximal terminus is generally the terminus of one polynucleotide that is closer to the other polynucleotide. In some non-limiting instances of template-dependent ligation, the proximal termini of both polynucleotides are hybridized adjacently to each other.

"Support", as used herein, refers to a structure or matrix on or in which ligation reagents, e.g., nucleic acid molecules, microparticles, and the like may be immobilized so that they are significantly or entirely prevented from diffusing freely or moving with respect to one another. The reagents can for example be placed in contact with the support, and optionally covalently or noncovalently attached or partially/completely embedded A "universal base", as used herein, is a base that is complementary to more than one other base. Fully universal bases can pair with any of the bases typically found in naturally occurring nucleic acids. The base need not be equally capable of pairing with each of the naturally occurring bases. Alternatively, the universal base may pair only or selectively with two or more bases but not all bases. Optionally the universal base pairs only or selectively with purines, or alternatively with pyrimidines. If so desired, two or more universal bases can be included at a particular position in a probe. A number of universal bases are known in the art including, but not limited to, inosine, hypoxanthine, 3-nitropyrrole, 4-nitroindole, 5-nitroindole, 4-nitrobenzimidazole, 5-nitroindazole, 8-aza-7-deazaadenine, 6H,8H-3,4-dihydropyrimido[4,5-c][1,2]oxazin-7-one, 2-amino-6-methoxyaminopurine, etc. Hypoxanthine is one preferred fully universal base. Nucleosides comprising hypoxanthine include, but are not limited to, inosine, isoinosine, 2'-deoxyinosine, and 7-deaza-2'-deoxyinosine, 2-aza-2'deoxyinosine.

"Purified" generally refers to isolation of a substance (compound, polynucleotide, protein, polypeptide, polypeptide composition) such that the substance comprises a significant percent, such as a higher proportion than it is naturally found (e.g., greater than 2%, greater than 5%, greater than 10%, greater than 20%, greater than 50%, or more, sometimes more than 90%, 95% or 99%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. "Isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original or naturally-occurring environment of the polynucleotide.

Exemplary ligases comprise a polypeptide. The terms "polypeptide," "peptide" and "protein" are used interchangeably herein to refer to a polymer of amino acid residues, or any variant or functional fragment thereof. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" includes naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Variants or derivatives of a given nucleotide sequence or polypeptide sequence are optionally conservatively modified variants. With respect to particular nucleic acid sequences, conservatively modified variants refers to those nucleic acids which encode identical or essentially identical amino acid sequences, or where the nucleic acid does not encode an amino acid sequence, to essentially identical sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. (see e.g., Creighton, Proteins (1984)).

Sequence identity (also called homology) refers to similarity in sequence of two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 90% identity at the amino acid level or at the nucleotide level. This definition also refers to the complement of a test sequence. Preferably, the identity exists over a region that is at least about 25, 50, or 100 residues in length, or across the entire length of at least one compared sequence. A preferred algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements specifically hybridize to each other under stringent conditions, such as those described herein. Nucleic acids that do not specifically hybridize to each other under stringent conditions are still substantially identical if the polypeptides which they encode are substantially identical.

Two polynucleotides selectively (or specifically) hybridize to each other if they bind significantly or detectably to each other under stringent hybridization conditions when present in a complex polynucleotide mixture such as total cellular or library DNA. For selective or specific hybridization, a positive signal is at least two times background, preferably 10 times background hybridization. Optionally, stringent conditions are selected to be about 5-10° C. lower than the thermal melting point for the specific sequence at a defined ionic strength pH. Stringent conditions are optionally in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary stringent hybridization conditions can be as following: 50% formamide, 5.times.SSC, and 1% SDS, incubating at 42° C., or, 5.times.SSC, 1% SDS, incubating at 65° C., with wash in 0.2.times.SSC, and 0.1% SDS at 65° C.

DETAILED DESCRIPTION

Among other novel and surprising information presented herein, the novel and surprising enzymatic ligation of short polynucleotides is presented herein.
1) Ligations Ligation herein refers to the enzymatic formation of a covalent bond between the termini of two or more or polynucleotides strands. "Ligation" involves the formation of a covalent bond or linkage between the 5' and 3' termini of two or more nucleic acids, e.g. oligonucleotides and/or polynucleotides, optionally in a template-driven reaction. The nature of the bond or linkage may vary widely and the ligation is preferably achieved enzymatically. The nature of the bond or linkage can vary widely. Non-limiting exemplary ligations are carried out enzymatically to form a phosphodiester linkage between a 5' terminal nucleotide of a polynucleotide strand with a 3' terminal nucleotide of a polynucleotide.

The ligation can be one or more of the following types of ligation described herein. A first type of enzymatic ligation involves the formation of a covalent bond between a first terminus of a first polynucleotide strand and a second different terminus of a second polynucleotide strand. The first and second polynucleotide termini can be on different polynucleotide strands, or can both be on the same polynucleotide strand (resulting in circularization). Optionally, the first and second polynucleotide strands are not both hybridized to a third polynucleotide. Optionally, the termini of the first and second polynucleotide strand are joined irrespective of their sequences (e.g., blunt-end ligation, or non-homologous end joining) In another variation, two double-stranded polynucleotides with protruding single-stranded portions that are complementary to each other can be ligated (e.g., cohesive-end ligation). A third type of ligation (template-dependent ligation) is described further below.

In any one of the methods described herein, the polynucleotide strands can be in single-stranded format or are hybridized to complementary strands in double-stranded format. In blunt-end ligation, both polynucleotide strands to be ligated are hybridized to two different complementary strands such that no overhang exists.

Methods are provided to ligate two polynucleotides. An exemplary ligation method achieves ligation between a first terminus of a first polynucleotide sequence and a second terminus of a second polynucleotide sequence. For ease of reference, the first polynucleotide sequence is called the "initializing probe" or "primer," the second polynucleotide called the "extension probe" or "probe." A third polynucleotide sequence that is optionally present (e.g., in template-dependent ligation) is termed the template or target sequence. Any one or more of the primer (initializing probe), probe (extension probe) and/or template sequences can be located on the same polynucleotide strand, or on different polynucleotide strands. In a one-strand system, the primer, probe and template are all on the same polynucleotide strand. In an example of a two-strand system, either the probe or primer (but not both) are on the same strand as the template (e.g., hybridization between the template sequence and the primer or probe sequences forms a stem-loop structure or hairpin). In another example of a two-strand system, the probe or primer are both on the same strand. In a three-strand system, the template, primer and probe are all on separate polynucleotide strands. Any ligation method described herein can be performed in a one-strand, two-strand or three-strand system.

Optionally, ligation converts a linear polynucleotide strand into a circular polynucleotide strand (e.g., in a one-stranded to two-stranded system). Optionally, ligation reduces the number of polynucleotide strands by one (e.g., in a two-stranded or three-stranded system).

Ligation optionally creates a bond between a terminal nucleotide of the probe with the terminal nucleotide of the primer. Optionally, the proximal terminus of the primer and/or probe is ligated. The terminal nucleotide of the primer can be the 5' terminal nucleotide and the terminal nucleotide of the extension probe can be the 3' terminal nucleotide. Alternatively, the terminal nucleotide of the primer can be the 3' terminal nucleotide and the terminal nucleotide of the extension probe can be the 5' terminal nucleotide. The 5' terminus of a polynucleotide for example has the fifth carbon in the sugar-ring of the deoxyribose or ribose at its terminus, optionally with a phosphate group attached to it, where the phosphate group is capable of forming a phosphodiester bond with a 3' terminal nucleotide. The 3' terminal nucleotide optionally has a 3'-hydroxyl group that is capable of forming a phosphodiester bond with a 5' terminal nucleotide. Ligation optionally results in the formation of a phophodiester bond.

Any of the polynucleotides no matter how designated (e.g., as "probes" or "primers" or "templates") can be of any sequence, any length, in any form and from any source. The polynucleotides can comprise a naturally-occurring sequence or be highly homologous to a naturally-occurring sequence, and/or derived from a naturally occurring sequence. The naturally occurring sequence can be any portion of a gene, a regulatory sequence, genomic DNA or fragment, cDNA, RNA including mRNA and rRNA, or others. The polynucleotides can optionally comprise any artificial sequence as well. The polynucleotide can be derived or obtained from a sample such as a diagnostic sample. The polynucleotide can be a secondary product of a reaction—for example a ligation product from a ligation reaction or assay such as those described herein, an extended probe from a PCR reaction, or PCR amplification product, ("amplicon"), the product of an invasive cleavage reaction, etc. The polynucleotide can have a 5' phosphate, or can alternatively lack a 5' phosphate.

The ligation product of any one reaction can optionally be subjected to further ligation and/or non-ligation reactions in turn. For example, the ligation product can be used as the primer (initializing probe) or extension probe and/or template in a subsequent ligation. Also for example, it can be used as a template and/or primer for a polymerase extension reaction, such as in PCR. The probe, primer, template and/or ligation product optionally can be subjected to any one or more modifications before or after ligation. For example, the probe, primer, template and/or ligation product can be cleaved enzymatically or chemically (for example at scissile linkages), treated with exo- or endonucleases, kinases, phosphatases, etc. The ends of a double-stranded product can be blunt-ended or filled in, capped, or adenylated, etc.

Optionally, the probe is not more than 20 consecutive nucleotides long, for example not more than 15, 12, 10, 8, 7 consecutive nucleotides, preferably not more than 6, 5, 4 3, or 2 consecutive nucleotides. Optionally, the probe is at least 2, 3, 4, 5, 6 or 7 nucleotides long. In some instances the probe is from any of the specified minimum lengths (e.g., 2, 3, 4, 5, 6 or 7 nucleotides long) and is not more than 20, 15, 12, 10, 8, 7 nucleotides, preferably not more than 6, 5, 4 3, or 2 nucleotides. In some examples, the probe is a 2-mer, 3-mer, 4-mer, 5-mer, 6-mer, 7-mer, 8-mer, 9-mer, 10-mer, 11-mer, 12-mer, 13-mer, 14-mer, 15-mer or 20-mer, or any combination of such oligonucleotides.

Optionally, the primer is not more than 20 consecutive nucleotides long, for example not more than 15, 12, 10, 8, 7 consecutive nucleotides, preferably not more than 6, 5, 4, 3, or 2 consecutive nucleotides. In some examples, the primer is one or more 2-mer, 3-mer, 4-mer, 5-mer, 6-mer, 7-mer, 8-mer, 9-mer, 10-mer, 11-mer, 12-mer, 13-mer, 14-mer, 15-mer or 20-mer, or any combination of such oligonucleotides.

It should be understood that the probe or primer (or template, if present) can be "mixed" or "composite," i.e., comprising a mixture of one or more polynucleotides of different sequences.

Optionally, the ligation is performed using CV ligase in combination with one or more probes that is at least 3 nucleotides long and not more than 6 or 5 nucleotides long. Optionally, the one or more probes are at least 3 nucleotides long and not more than 4 nucleotides long. In other examples the one or more probes are at least 4 nucleotides long and not more than 5 nucleotides long. Alternatively all of the one or more probes probe can be 3-mers. Otherwise all of the one or more probes probe can be 4-mers.

When the ligation is performed using DLX, DLXd, DLXd2 ligase, then optionally ligation is performed with one or more probes that is at least 2 or 3 nucleotides long and not more than 6 or 5 nucleotides long. Optionally, the one or more probes are at least 3 nucleotides long and not more than 4 nucleotides long. In other examples the one or more probes are at least 4 nucleotides long and not more than 5 nucleotides long. Alternatively all of the one or more probes probe can be 3-mers. Otherwise all of the one or more probes probe can be 4-mers.

The ligation can be a template-dependent ligation. In template-dependent ligation, ligation between a primer sequence and a probe sequence occurs upon hybridization of at least a portion of either or both sequences to a template sequence. In some instances, both probes must hybridize to the template for significant ligation to occur. In a typical example, template-dependent ligation cannot take place unless both polynucleotides are hybridized to the template sequence. The portion of the primer or probe that is hybridized to the target sequence is generally at least two nucleotides long. The hybridized portion is optionally not more than 20 consecutive nucleotides long, for example not more than 15, 12, 10, 8, 7 consecutive nucleotides, preferably not more than 6, 5, 4, 3, or 2 consecutive nucleotides. The hybridized portion is optionally a terminal portion of the first or second polynucleotide (e.g., a portion that includes the 5' or 3' terminal nucleotide). For example, the hybridized portion can consist of the terminal 2, 3, 4, 5, 6, 7, 8, 10, 15 or 20 nucleotides of the 5' or 3' end.

Optionally, ligation occurs when no mismatch is present within one or more hybridized portions. In other cases, ligation occurs when one, two or three mismatches can be present within one or more hybridized portions. In some cases ligation does not occur when the terminal nucleotide and/or second-most terminal nucleotide and/or third-most terminal nucleotide is mismatched. As mentioned, the terminal nucleotides can be the 5'- or 3'-terminal nucleotides of the polynucleotide.

Optionally the template, if present, is not more than 11 nucleotides in length, for example not more 10, 9, 8, 7, 6, 5, or 4 nucleotides. Optionally the template is one or more N-mers, where N is 4, 5, 6, 7, 8, 9, 10 or 11.

Optionally, template-dependent ligation of a nucleic acid comprises: a) providing a first oligonucleotide having less than 6 nucleotides; b) providing a second oligonucleotide; c) bringing the 3' termini of one of the first and second oligonucleotides into proximity with the 5' termini of the other oligonucleotide; and d) ligating the first and the second oligonucleotides. Optionally, the first oligonucleotide has a length of 5 nucleotides. Optionally, the first oligonucleotide has a length of 4 nucleotides. Optionally, the first oligonucleotide has a length of 3 nucleotides. Optionally, the ligation is performed using a small-footprint ligase (SFL). Optionally, the second oligonucleotide includes a sequence complementary to a portion of a template nucleic acid. Optionally, the second oligonucleotide is hybridized to the template nucleic acid at the region of complementarity. Optionally, the first oligonucleotide has a sequence complementary to the template nucleic acid. Optionally, the first oligonucleotide is hybridized to the template nucleic acid at the region of complementarity, and wherein a terminus of the first oligonucleotide is adjacent to a terminus of the second oligonucleotide.

In some variations, (e.g., "nick ligation" or "template-dependent" ligation), both primer and probe must hybridize adjacently to each other on the template for ligation to occur. Optionally, the probe and primer are adjacently hybridized and can be ligated only when a terminal nucleotide of the primer is hybridized to a first nucleotide of the template and a terminal nucleotide of the extension probe is hybridized to a second nucleotide of the template, where the first and second nucleotides on the template are not separated by an intervening nucleotide of the template. In other embodiments, intervening nucleotides may be present between the first and second nucleotides on the template (optionally a few nucleotides, e.g., not more than 1, 2, 3, 5, 10 or 15 nucleotides). In such embodiments, a "gap-filling" step can be performed to extend the 3' terminus of the probe or probe before it can be ligated to the 5' terminus of the other.

Optionally, at least one of the probe, the template (if the ligation is template-dependent) and/or the primer is immobilized while another of these three is labeled. For example in ligation sequencing the template and/or primer can be immobilized and the probe can be labeled.

A probe can for example be N nucleotide residues in length, where N is from 2 to 10, e.g., 2, 3, or 4. N can also be less than 6, for example if the proximal terminus of the probe is its 3' terminus.

Optionally, ligation is a "forward" ligation (i.e., ligation of the 3' terminus of the probe to the 5' terminus of the primer). Alternatively, "reverse" ligation can be achieved, where the 5' terminus of the probe is ligated to the 3' terminus of the primer.

A probe can also be of length N, and can comprise a proximal portion that is perfectly hybridized to the template and is L nucleotides long, where the probe's L+1th nucleotide is mismatched with the template. L can be, for example, from 2 to 8, and furthermore can be less than 6 if the proximal terminus of the probe is its 3' terminus. In other embodiments, L can be 2, 3, 4, 5, 6, 7 or 8.

The ligation can be repeated at least once, for any desired number of cycles. Optionally, any ligation product of a previous ligation reaction is used as the primer of a next ligation. Optionally, all ligations extend the ligation product in the same direction. For example, all ligation reactions can be forward ligations or all can be reverse ligations. In other embodiments, some ligations can be forward and some reverse. Optionally any unligated primer is rendered unligatable before initiating the next ligation. If so desired (e.g., in ligation sequencing), the method further comprises detecting whether the probe has ligated to the primer before repeating the next ligation reaction.

Where so desired, any ligation product of the previous ligation reaction can be used as the template of the next ligation reaction, e.g., in a ligase chain reaction.

Optionally, the 5' end of the probe less than 6 nucleotides long is ligated to the 3' end of the primer by a SFL such as CV ligase. For example the probe is 2, 3 or 4 nucleotides long. If so desired, the primer is also a short oligonucleotides. For example, the primer can be less than 6 nucleotides, e.g., 3 or 4 nucleotides long.

The ligation should produce a significant or detectable amount of ligation product. Optionally, the efficiency of ligation is at least 5%, sometimes at 10%, 20%, 30%, 50%, 60%, 70%, 75%, 80%, 85%, 90% or 95%. The efficiency of ligation (in percentage terms) can in some embodiment be regarded as the percent portion of ligation reagent that is ligated to form ligation product at the end of the ligation reaction. Efficiency is optionally determined after a ligation reaction has reach equilibrium such that increasing the ligation time will not result in a substantial increase of ligation product formed. Generally, a ligation reaction can be said to have reached equilibrium after 20 minutes. For example, a ligation reaction in which 90% of the primer or probe is ligated can be said to have proceeded at 90% efficiency. The ligation reagent used to measure ligation efficiency is optionally whichever reagent that is in lower concentration than the others. Optionally, the other reagents and conditions are non-limiting to the ligation efficiency (e.g., other reagents are present in excess or at a concentration that is at least equal to or higher than the limiting reagent).

In some embodiments, the SFL can ligate a short probe that is shorter than N nucleotides at least X % as efficiently as the SFL can ligate the corresponding N-mer. N is optionally 4, 5, 6, 7, 8, 10, 12, 15 or 20. In some embodiments N is 6 or 7. X is optionally at least 30%, 50%, 60%, 70%, 80% or 90%. In some embodiments of template-dependent ligation, the length of short probe is Y residues, and the Y proximal residues of the corresponding longer N-mer are identical to the probe, and the distal N-Y residues of the corresponding longer N-mer are perfectly complementary to the template. Y is for example 2, 3, 4, 5 or 6.

In some embodiments, the SFL can ligate a short probe that is shorter than N nucleotides when the short probe is conjugated to a dye approximately as efficiently as the SFL can ligate the unconjugated probe. N is optionally 4, 5, 6, 7, 8, 10, 12, 15 or 20. In some embodiments N is 6 or 7. In other embodiments, the SFL can ligate the short probe conjugated to a dye at least 30%, 50%, 60%, 70%, 80% or 90% as efficiently as the SFL can ligate the unconjugated probe. Exemplary dyes include Cy5.

It is understood that ligation efficiency (whether expressed in absolute or relative terms) may increase or decrease depending on the exact reaction conditions used.

Optionally, the ligation efficiency is measured when the primer or probe is at a concentration of about $10^{-9}$ to $10^{-4}$ M, for example at about $10^{-8}$, $10^{-7}$, $10^{-6}$, or $10^{-5}$ M. In certain applications, for example sequencing applications, a working concentration often used in the range of $10^{-8}$ to $10^{-5}$, e.g., $10^{-7}$ or $10^{-6}$ M of probe. Where a mixture of probes are used, the probe concentration is the concentration of only those probes that are capable of being ligated in that particular ligation reaction (e.g., probe(s) complementary to the template). Thus other probes that are not capable of participating in the ligation reaction are optionally not considered when calculating the concentration of the probe of interest. Optionally, the concentration of probe is between 1 picomolar and 1 millimolar, for example about 0.01-100 μM, e.g., 1-10 μM, e.g., 1-5 μM. In the case of 2-mers, the concentration is optionally increased to 10-1000 μM, for example about 100 μM. Optionally, the concentration of ligase is between 1 picomolar and 1 millimolar, e.g., 1-2 micromolar. Optionally, the ligation assay is performed at 15-35° C., for example 15° C., 20° C., 25° C. or 30° C. Where two or more reagents are involved and the concentration of one particular reagent is specified, the other reagents are optionally in excess and/or not at a concentration that is limiting for the ligation.

Ligation can be performed under in vitro conditions that have been experimentally determined to be suitable or optimal for ligase activity. Preferably, the reaction conditions of choice are (i) substantially similar to in vivo or physiological conditions in which a naturally-occurring form of the ligase being used is active, or (ii) have been experimentally determined to result in a ligation efficiency that is comparable to or better than the efficiency obtained using conditions of type (i). If exemplary in vitro ligation conditions are specified herein for a particular SFL, then substantially similar reaction conditions are generally appropriate for that particular ligase. In other embodiments, the conditions are such that the reference ligation assay produces significant or detectable ligation within 30 minutes, within 10 minutes, within 1 minute, or within ten seconds. Another non-limiting example of a significant or detectable efficiency of ligation generates in the range of 100 pM of ligation product, optionally about 1000 pM or 10,000 pM.

Optionally, relative efficiency can be expressed as relative percent efficiency, which can be calculated as AB×100, where A is the percent of test reagent (e.g., probe) ligated in a test assay and B is the percent of the reference reagent (e.g., reference probe) that is ligated in a reference assay. Where the relative efficiency of ligation is specified in comparative or relative terms by comparison to a reference ligation assay, it is implicit that all other reagents and conditions (e.g., temperature, concentration of all reagents, pH, concentration of requisite ions such as Mg++ and Mn++, concentration of requisite cofactors such as NAD and/or ATP, salts, buffers, molar concentrations of all reagents, including enzyme, template, probe, primer, oligonucleotides, etc) are otherwise kept identical. For example, a proviso that a SFL can ligate a short (e.g., less than 6 nucleotides) probe at least X % as efficiently as the SFL can ligate a corresponding octanucleotide, can be taken to mean that the two different ligation assays all reagents except for the probes (e.g., primer, template, enzymes and any other reagents) and all reaction conditions (e.g., temperature, reagent concentrations, concentrations of any other reagents, etc) are kept the same for practical purposes.

Optionally, the ligase has a better ligation efficiency than T4 DNA ligase, for example in any method described herein. In an embodiment, the ligation efficiency is higher than that of T4 DNA ligase for the same mix of probe(s), primer(s) and template(s), in any ligation method and chosen conditions, including any described herein. The ligation efficiency is for example at least 5% higher than T4 ligase, optionally at least 10%, 15% or 20% higher. The increase in efficiency should be statistically reliable and significant, e.g., with a confidence interval of at least 95%, 99%, 99.9%, 99.99%, or 99.999999%. In an example, the SFL shows higher efficiency than T4 DNA ligase when ligating a probe of 8 nucleotides or less to a primer in the forward or reverse direction. The ligase, template, probe, primer and/or ligation assay conditions are for example any described herein.

The ligase optionally has good ligation fidelity. The ligation fidelity can be assessed as the percentage of incorrect ligation events for a given combination of ligase, template, primer and probe. An incorrect ligation event is one in which the probe or the primer is not perfectly complementary to the template, or the ligation product is not perfectly complementary to the template. In an embodiment, the ligation fidelity is higher than that of T4 DNA ligase for the same mix of probe(s), primer(s) and template(s), in any ligation method and chosen conditions, including any described herein. The ligation fidelity is for example at least 5% higher than T4 ligase, optionally at least 10%, 15% or 20% higher. The increase in fidelity should be statistically reliable and significant, e.g., with a confidence interval of at least 95%, 99%, 99.9%, 99.99%, or 99.999999%. In an example, the SFL shows higher fidelity than T4 DNA ligase when ligating a probe of 8 nucleotides or less to a primer in the forward or reverse direction. The ligase, template, probe, primer and/or ligation assay conditions are for example any described herein.

2) Small Footprint Ligases

Optionally, the enzymatic ligation of polynucleotides is achieved by a small footprint ligase (SFL). For example, any ligation method provided herein can use a ligase shown in Table 1A, 1B or 1C. A SFL is a ligase that can ligate short polynucleotides. As used herein, the term "ligase" is intended to include any fragment or variant or derivative of that ligase. The fragment or variant or derivative optionally possesses one or more functional activities of a ligase. A SFL optionally comprises a polypeptide having any one or more of the following activities: (1) nucleophilic attack on ATP or $NAD^+$ resulting in release of PPi or NMN and formation of a covalent ligase-adenylate intermediate; (2) transferring the adenylate to the 5'-end of the 5'-phosphate-terminated DNA strand to form DNA-adenylate (e.g., 5'-phosphate oxygen of the DNA strand attacks the phosphorus of ligase-adenylate); and (3) formation of a covalent bond joining the polynucleotide termini and liberation of AMP (e.g., by the attack by the 3'-OH on DNA-adenylate). Optionally, the SFL can mediate any one or more of the following bond transformations: from phosphoanhydride (ATP) to phosphoramidate (ligase-adenylate); from phosphoramidate (ligase-adenylate) to phosphoanhydride (DNA-adenylate); or from phosphoanhydride (DNA-adenylate) to phosphodiester (sealed DNA). Thus, exemplary SFLs can comprise a polypeptide sequence that is homologous to or a variant of a known SFL sequence or any portion thereof. Exemplary SFLs optionally have amino acid sequence identity of at least 70%, optionally at least 85%, optionally at least 90, 95%, 97% or 99%, with a known ligase or known SFL.

Representative examples of SFLs include CV ligase, DLX, DLXd, DLXd2 and MnM ligase. A preferred SFL is *Chlorella* Virus ligase. Some exemplary ligases are identified and their GI or accession numbers are provided in Table 1A below:

TABLE 1A

| Organism | Protein name | Accession |
| --- | --- | --- |
| PRK08224 | | |
| B. Acidobacteria | | |
| *Candidatus Koribacter versatilis* Ellin345Candidatus Koribacter (1 proteins) | ATP-Dependent DNA Ligase | YP_592504 |
| *Candidatus Solibacter usitatus* Ellin6076Candidatus Solibacter (1 proteins) | ATP-Dependent DNA Ligase | YP_826317 |
| C. Actinobacteria | | |
| *Acidothermus cellulolyticus* 11BAcidothermus (1 proteins) | ATP-Dependent DNA Ligase | YP_873134 |
| *Actinosynnema mirum* DSM 43827Actinosynnema (1 proteins) | ATP-Dependent DNA Ligase | YP_003099374 |
| *Arthrobacter aurescens* TC1Arthrobacter (3 proteins) | ATP-Dependent DNA Ligase | YP_949544 |
| *Arthrobacter chlorophenolicus* A6Arthrobacter (3 proteins) | ATP-Dependent DNA Ligase | YP_002489901 |
| *Arthrobacter* sp. FB24Arthrobacter (3 proteins) | ATP-Dependent DNA Ligase | YP_833558 |
| *Beutenbergia cavernae* DSM 12333Beutenbergia (1 proteins) | ATP-Dependent DNA Ligase | YP_002880505 |
| *Catenulispora acidiphila* DSM 44928Catenulispora (2 proteins) | ATP-Dependent DNA Ligase | YP_003116519 |
| *Catenulispora acidiphila* DSM 44928Catenulispora (2 proteins) | ATP-Dependent DNA Ligase | YP_003116565 |
| *Frankia alni* ACN14aFrankia (2 proteins) | ATP-Dependent DNA Ligase | YP_712338 |
| *Frankia* sp. EAN1pecFrankia (2 proteins) | ATP-Dependent DNA Ligase | YP_001509433 |
| *Kineococcus radiotolerans* SRS30216Kineococcus (1 proteins) | ATP-Dependent DNA Ligase | YP_001360406 |
| *Kytococcus sedentarius* DSM 20547Kytococcus (1 proteins) | ATP-Dependent DNA Ligase | YP_003149340 |
| *Mycobacterium abscessus* ATCC 19977Mycobacterium (26 proteins) | ATP-Dependent DNA Ligase | YP_001701033 |

TABLE 1A-continued

| Organism | Protein name | Accession |
|---|---|---|
| *Mycobacterium avium* 104Mycobacterium (26 proteins) | ATP-Dependent DNA Ligase | YP_879648 |
| *Mycobacterium avium* subsp. *paratuberculosis* K-10Mycobacterium (26 proteins) | ATP-Dependent DNA Ligase | NP_959275 |
| *Mycobacterium gilvum* PYR-GCKMycobacterium (26 proteins) | ATP-Dependent DNA Ligase | YP_001132524 |
| *Mycobacterium gilvum* PYR-GCKMycobacterium (26 proteins) | ATP-Dependent DNA Ligase | YP_001132543 |
| *Mycobacterium marinum* MMycobacterium (26 proteins) | ATP-Dependent DNA Ligase | YP_001853525 |
| *Mycobacterium smegmatis* str. MC2 155Mycobacterium (26 proteins) | ATP-Dependent DNA Ligase | YP_890520 |
| *Mycobacterium smegmatis* str. MC2 155Mycobacterium (26 proteins) | ATP-Dependent DNA Ligase | YP_890521 |
| *Mycobacterium* sp. JLSMycobacterium (26 proteins) | ATP-Dependent DNA Ligase | YP_001073538 |
| *Mycobacterium* sp. JLSMycobacterium (26 proteins) | ATP-Dependent DNA Ligase | YP_001073546 |
| *Mycobacterium* sp. JLSMycobacterium (26 proteins) | ATP-Dependent DNA Ligase | YP_001073574 |
| *Mycobacterium ulcerans* Agy99Mycobacterium (26 proteins) | ATP-Dependent DNA Ligase | YP_907815 |
| *Mycobacterium vanbaalenii* PYR-1Mycobacterium (26 proteins) | ATP-Dependent DNA Ligase | YP_956315 |
| *Mycobacterium vanbaalenii* PYR-1Mycobacterium (26 proteins) | ATP-Dependent DNA Ligase | YP_956321 |
| *Mycobacterium tuberculosis* H37RaMycobacterium (26 proteins) | ATP-Dependent DNA Ligase | YP_001285120 |
| *Mycobacterium tuberculosis* H37RvMycobacterium (26 proteins) | ATP-Dependent DNA Ligase | NP_218248 |
| *Mycobacterium bovis* AF2122/97Mycobacterium (26 proteins) | ATP-Dependent DNA Ligase | NP_857396 |
| *Mycobacterium bovis* BCG str. Pasteur 1173P2Mycobacterium (26 proteins) | ATP-Dependent DNA Ligase | YP_979871 |
| *Mycobacterium bovis* BCG str. Tokyo 172Mycobacterium (26 proteins) | ATP-Dependent DNA Ligase | YP_002646832 |
| *Mycobacterium tuberculosis* CDC1551Mycobacterium (26 proteins) | ATP-Dependent DNA Ligase | NP_338389 |
| *Mycobacterium tuberculosis* F11Mycobacterium (26 proteins) | ATP-Dependent DNA Ligase | YP_001289690 |
| *Mycobacterium tuberculosis* KZN 1435Mycobacterium (26 proteins) | ATP-Dependent DNA Ligase | YP_003033779 |
| *Mycobacterium* sp. KMSMycobacterium (26 proteins) | ATP-Dependent DNA Ligase | YP_940984 |
| *Mycobacterium* sp. MCSMycobacterium (26 proteins) | ATP-Dependent DNA Ligase | YP_642076 |
| *Mycobacterium* sp. KMSMycobacterium (26 proteins) | ATP-Dependent DNA Ligase | YP_941006 |
| *Mycobacterium* sp. MCSMycobacterium (26 proteins) | ATP-Dependent DNA Ligase | YP_642099 |
| *Nakamurella multipartita* DSM 44233Nakamurella (1 proteins) | ATP-Dependent DNA Ligase | YP_003200226 |
| *Nocardia farcinica* IFM 10152Nocardia (1 proteins) | ATP-Dependent DNA Ligase | YP_118771 |
| *Nocardioides* sp. JS614Nocardioides (1 proteins) | ATP-Dependent DNA Ligase | YP_922117 |
| *Rhodococcus erythropolis* PR4Rhodococcus (3 proteins) | ATP-Dependent DNA Ligase | YP_002768423 |
| *Rhodococcus jostii* RHA1Rhodococcus (3 proteins) | ATP-Dependent DNA Ligase | YP_705046 |
| *Rhodococcus opacus* B4Rhodococcus (3 proteins) | ATP-Dependent DNA Ligase | YP_002782360 |
| *Saccharopolyspora erythraea* NRRL 2338Saccharopolyspora (1 proteins) | ATP-Dependent DNA Ligase | YP_001104098 |
| *Salinispora arenicola* CNS-205Salinispora (2 proteins) | ATP-Dependent DNA Ligase | YP_001536378 |
| *Salinispora tropica* CNB-440Salinispora (2 proteins) | ATP-Dependent DNA Ligase | YP_001158390 |
| *Streptomyces avermitilis* MA-4680Streptomyces (3 proteins) | ATP-Dependent DNA Ligase | NP_822873 |
| *Streptomyces coelicolor* A3(2)*Streptomyces* (3 proteins) | ATP-Dependent DNA Ligase | NP_630780 |
| *Streptomyces griseus* subsp. *griseus* NBRC 13350Streptomyces (3 proteins) | ATP-Dependent DNA Ligase | YP_001822536 |
| F. Chlamydiae/Verrucomicrobia | | |
| *Opitutus terrae* PB90-1Opitutus (1 proteins) | ATP-Dependent DNA Ligase | YP_001821013 |

TABLE 1A-continued

| Organism | Protein name | Accession |
|---|---|---|
| N. Alphaproteobacteria | | |
| *Bradyrhizobium japonicum* USDA 110*Bradyrhizobium* (3 proteins) | ATP-Dependent DNA Ligase | NP_771853 |
| *Bradyrhizobium* sp. BTAi1*Bradyrhizobium* (3 proteins) | ATP-Dependent DNA Ligase | YP_001236299 |
| *Bradyrhizobium* sp. ORS278*Bradyrhizobium* (3 proteins) | ATP-Dependent DNA Ligase | YP_001202307 |
| *Chelativorans* sp. BNC1*Chelativorans* (1 proteins) | ATP-Dependent DNA Ligase | YP_675242 |
| *Mesorhizobium loti* MAFF303099*Mesorhizobium* (2 proteins) | ATP-Dependent DNA Ligase | NP_108245 |
| *Mesorhizobium loti* MAFF303099 (plasmid)*Mesorhizobium* (2 proteins) | ATP-Dependent DNA Ligase | NP_109531 |
| *Methylocella silvestris* BL2*Methylocella* (1 proteins) | ATP-Dependent DNA Ligase | YP_002363964 |
| *Nitrobacter hamburgensis* X14*Nitrobacter* (1 proteins) | ATP-Dependent DNA Ligase | YP_579055 |
| *Phenylobacterium zucineum* HLK1*Phenylobacterium* (1 proteins) | ATP-Dependent DNA Ligase | YP_002131547 |
| *Rhizobium leguminosarum* bv. *trifolii* WSM2304 (plasmid)*Rhizobium* (2 proteins) | ATP-Dependent DNA Ligase | YP_002279148 |
| *Rhizobium* sp. NGR234 (plasmid)*Rhizobium* (2 proteins) | ATP-Dependent DNA Ligase | YP_002823307 |
| *Sinorhizobium medicae* WSM419 (plasmid)*Sinorhizobium* (2 proteins) | ATP-Dependent DNA Ligase ATP-Dependent DNA Ligase | YP_001312861 |
| *Sinorhizobium meliloti* 1021 (plasmid)*Sinorhizobium* (2 proteins) | ATP-Dependent DNA Ligase | NP_436551 |
| P. Deltaproteobacteria | | |
| *Anaeromyxobacter dehalogenans* 2CP-1*Anaeromyxobacter* (5 proteins) | ATP-Dependent DNA Ligase | YP_002491286 |
| *Anaeromyxobacter dehalogenans* 2CP-C*Anaeromyxobacter* (5 proteins) | ATP-Dependent DNA Ligase | YP_464028 |
| *Anaeromyxobacter* sp. Fw109-5*Anaeromyxobacter* (5 proteins) | ATP-Dependent DNA Ligase | YP_001378773 |
| *Anaeromyxobacter* sp. Fw109-5*Anaeromyxobacter* (5 proteins) | ATP-Dependent DNA Ligase | YP_001381200 |
| *Anaeromyxobacter* sp. K*Anaeromyxobacter* (5 proteins) PRK09125 | ATP-Dependent DNA Ligase | YP_002133229 |
| O. Betaproteobacteria | | |
| *Acidovorax* sp. JS42*Acidovorax* (1 proteins) | DNA ligase | YP_986978 |
| *Aromatoleum aromaticum* EbN1*Aromatoleum* (1 proteins) | DNA ligase | YP_161050 |
| *Azoarcus* sp. BH72*Azoarcus* (1 proteins) | DNA ligase | YP_934633 |
| *Candidatus Accumulibacter phosphatis* clade IIA str. UW-1*Candidatus Accumulibacter* (1 proteins) | DNA ligase | YP_003169249 |
| *Dechloromonas aromatica* RCB*Dechloromonas* (1 proteins) | DNA ligase | YP_284461 |
| *Diaphorobacter* sp. TPSY*Diaphorobacter* (1 proteins) | DNA ligase | YP_002553689 |
| *Herminiimonas arsenicoxydans**Herminiimonas* (1 proteins) | DNA ligase | YP_001100009 |
| *Leptothrix cholodnii* SP-6*Leptothrix* (1 proteins) | DNA ligase | YP_001791742 |
| *Methylibium petroleiphilum* PM1*Methylibium* (1 proteins) | DNA ligase | YP_001020556 |
| *Neisseria gonorrhoeae* FA 1090*Neisseria* (7 proteins) | DNA ligase | YP_209054 |
| *Neisseria gonorrhoeae* NCCP11945*Neisseria* (7 proteins) | DNA ligase | YP_002002827 |
| *Neisseria meningitidis* 053442*Neisseria* (7 proteins) | DNA ligase | YP_001598310 |
| *Neisseria meningitidis* FAM18*Neisseria* (7 proteins) | DNA ligase | YP_975951 |
| *Neisseria meningitidis* MC58*Neisseria* (7 proteins) | DNA ligase | NP_275038 |
| *Neisseria meningitidis* Z2491*Neisseria* (7 proteins) | DNA ligase | YP_002341892 |
| *Neisseria meningitidis* alpha14*Neisseria* (7 proteins) | DNA ligase | YP_003082363 |
| *Polaromonas naphthalenivorans* CJ2*Polaromonas* (2 proteins) | DNA ligase | YP_982249 |

TABLE 1A-continued

| Organism | Protein name | Accession |
|---|---|---|
| *Polaromonas* sp. JS666Polaromonas (2 proteins) | DNA ligase | YP_549233 |
| *Rhodoferax ferrireducens* T118Rhodoferax (1 proteins) | DNA ligase | YP_522700 |
| *Thauera* sp. MZ1TThauera (1 proteins) | DNA ligase | YP_002353773 |
| *Thiobacillus denitrificans* ATCC 25259Thiobacillus (1 proteins) | DNA ligase | YP_314570 |
| *Variovorax paradoxus* S110Variovorax (1 proteins) | DNA ligase | YP_002944627 |
| *Verminephrobacter eiseniae* EF01-2Verminephrobacter (1 proteins) | DNA ligase | YP_998235 |
| P. Deltaproteobacteria | | |
| *Desulfobacterium autotrophicum* HRM2Desulfobacterium (1 proteins) | LigA2 | YP_002604477 |
| *Myxococcus xanthus* DK 1622Myxococcus (1 proteins) | DNA ligase | YP_628883 |
| Q. Epsilonproteobacteria | | |
| *Arcobacter butzleri* RM4018Arcobacter (1 proteins) | ATP-dependent DNA ligase | YP_001489632 |
| *Campylobacter concisus* 13826Campylobacter (10 proteins) | ATP-dependent DNA ligase | YP_001467307 |
| *Campylobacter curvus* 525.92Campylobacter (10 proteins) | ATP-dependent DNA ligase | YP_001407695 |
| *Campylobacter fetus* subsp. *fetus* 82-40Campylobacter (10 proteins) | ATP-dependent DNA ligase | YP_892536 |
| *Campylobacter hominis* ATCC BAA-381Campylobacter (10 proteins) | ATP-dependent DNA ligase | YP_001406356 |
| *Campylobacter jejuni* RM1221Campylobacter (10 proteins) | ATP-dependent DNA ligase | YP_179811 |
| *Campylobacter jejuni* subsp. *doylei* 269.97Campylobacter (10 proteins) | ATP-dependent DNA ligase | YP_001398949 |
| *Campylobacter jejuni* subsp. *jejuni* 81-176Campylobacter (10 proteins) | ATP-dependent DNA ligase | YP_001001312 |
| *Campylobacter jejuni* subsp. *jejuni* 81116Campylobacter (10 proteins) | ATP-dependent DNA ligase | YP_001483144 |
| *Campylobacter jejuni* subsp. *jejuni* NCTC 11168Campylobacter (10 proteins) | ATP-dependent DNA ligase | YP_002345037 |
| *Campylobacter lari* RM2100Campylobacter (10 proteins) | ATP-dependent DNA ligase | YP_002574655 |
| *Sulfurimonas denitrificans* DSM 1251Sulfurimonas (1 proteins) | DNA ligase | YP_393098 |
| R. Gammaproteobacteria | | |
| *Actinobacillus succinogenes* 130ZActinobacillus (1 proteins) | ATP-dependent DNA ligase | YP_001344487 |
| *Aggregatibacter actinomycetemcomitans* D11S-1Aggregatibacter (2 proteins) | ATP-dependent DNA ligase | YP_003256304 |
| *Aggregatibacter aphrophilus* NJ8700Aggregatibacter (2 proteins) | ATP-dependent DNA ligase | YP_003007537 |
| *Alcanivorax borkumensis* SK2Alcanivorax (1 proteins) | ATP-dependent DNA ligase | YP_694422 |
| *Aliivibrio salmonicida* LFI1238Aliivibrio (3 proteins) | ATP-dependent DNA ligase | YP_002262821 |
| *Vibrio fischeri* ES114Aliivibrio (3 proteins) | ATP-dependent DNA ligase | YP_204833 |
| *Vibrio fischeri* MJ11Aliivibrio (3 proteins) | ATP-dependent DNA ligase | YP_002156265 |
| *Alteromonas macleodii* 'Deep ecotype'Alteromonas (1 proteins) | ATP-dependent DNA ligase | YP_002127707 |
| *Mannheimia succiniciproducens* MBEL55EBasfia (1 proteins) | ATP-dependent DNA ligase | YP_088131 |
| *Colwellia psychrerythraea* 34HColwellia (1 proteins) | ATP-dependent DNA ligase | YP_271053 |
| *Haemophilus influenzae* 86-028NPHaemophilus (3 proteins) | ATP-dependent DNA ligase | YP_248841 |
| *Haemophilus influenzae* PittEEHaemophilus (3 proteins) | ATP-dependent DNA ligase | YP_001290961 |
| *Haemophilus influenzae* PittGGHaemophilus (3 proteins) | ATP-dependent DNA ligase | YP_001293088 |
| *Haemophilus somnus* 129PTHistophilus (2 proteins) | ATP-dependent DNA ligase | YP_719536 |
| *Haemophilus somnus* 2336Histophilus (2 proteins) | ATP-dependent DNA ligase | YP_001783642 |
| *Idiomarina loihiensis* L2TRIdiomarina (1 proteins) | ATP-dependent DNA ligase | YP_156435 |
| *Marinobacter aquaeolei* VT8Marinobacter (1 proteins) | ATP-dependent DNA ligase | YP_960951 |

TABLE 1A-continued

| Organism | Protein name | Accession |
|---|---|---|
| *Marinomonas* sp. MWYL1Marinomonas (1 proteins) | ATP-dependent DNA ligase | YP_001341226 |
| *Photobacterium profundum* SS9Photobacterium (1 proteins) | ATP-dependent DNA ligase | YP_132765 |
| *Pseudoalteromonas atlantica* T6cPseudoalteromonas (2 proteins) | ATP-dependent DNA ligase | YP_659659 |
| *Pseudoalteromonas haloplanktis* TAC125Pseudoalteromonas (2 proteins) | ATP-dependent DNA ligase | YP_340675 |
| *Psychromonas ingrahamii* 37Psychromonas (1 proteins) | ATP-dependent DNA ligase | YP_942593 |
| *Shewanella amazonensis* SB2BShewanella (18 proteins) | ATP-dependent DNA ligase | YP_927870 |
| *Shewanella baltica* OS155Shewanella (18 proteins) | ATP-dependent DNA ligase | YP_001050227 |
| *Shewanella baltica* OS185Shewanella (18 proteins) | ATP-dependent DNA ligase | YP_001366044 |
| *Shewanella baltica* OS195Shewanella (18 proteins) | ATP-dependent DNA ligase | YP_001554317 |
| *Shewanella baltica* OS223Shewanella (18 proteins) | ATP-dependent DNA ligase | YP_002358357 |
| *Shewanella frigidimarina* NCIMB 400Shewanella (18 proteins) | ATP-dependent DNA ligase | YP_750174 |
| *Shewanella halifaxensis* HAW-EB4Shewanella (18 proteins) | ATP-dependent DNA ligase | YP_001673966 |
| *Shewanella loihica* PV-4Shewanella (18 proteins) | ATP-dependent DNA ligase | YP_001093713 |
| *Shewanella oneidensis* MR-1Shewanella (18 proteins) | ATP-dependent DNA ligase | NP_717802 |
| *Shewanella pealeana* ATCC 700345Shewanella (18 proteins) | ATP-dependent DNA ligase | YP_001502366 |
| *Shewanella piezotolerans* WP3Shewanella (18 proteins) | ATP-dependent DNA ligase | YP_002312387 |
| *Shewanella sediminis* HAW-EB3Shewanella (18 proteins) | ATP-dependent DNA ligase | YP_001474374 |
| *Shewanella* sp. ANA-3Shewanella (18 proteins) | ATP-dependent DNA ligase | YP_870036 |
| *Shewanella* sp. MR-4Shewanella (18 proteins) | ATP-dependent DNA ligase | YP_734321 |
| *Shewanella* sp. MR-7Shewanella (18 proteins) | ATP-dependent DNA ligase | YP_738313 |
| *Shewanella woodyi* ATCC 51908Shewanella (18 proteins) | ATP-dependent DNA ligase | YP_001760369 |
| *Shewanella putrefaciens* CN-32Shewanella (18 proteins) | ATP-dependent DNA ligase | YP_001183272 |
| *Shewanella* sp. W3-18-1Shewanella (18 proteins) | ATP-dependent DNA ligase | YP_963655 |
| *Thiomicrospira crunogena* XCL-2Thiomicrospira (1 proteins) | ATP-dependent DNA ligase | YP_391938 |
| *Vibrio cholerae* MJ-1236Vibrio (9 proteins) | ATP-dependent DNA ligase | YP_002878565 |
| *Vibrio parahaemolyticus* RIMD 2210633Vibrio (9 proteins) | DNA ligase | NP_797856 |
| *Vibrio splendidus* LGP32Vibrio (9 proteins) | DNA ligase | YP_002417130 |
| *Vibrio vulnificus* CMCP6Vibrio (9 proteins) | DNA ligase | NP_761477 |
| *Vibrio vulnificus* YJ016Vibrio (9 proteins) | DNA ligase | NP_934427 |
| *Vibrio cholerae* M66-2Vibrio (9 proteins) | DNA ligase | YP_002810248 |
| *Vibrio cholerae* O1 biovar El Tor str. N16961 Vibrio (9 proteins) | DNA ligase | NP_231182 |
| *Vibrio cholerae* O395Vibrio (9 proteins) | DNA ligase | YP_001217094 |
| *Vibrio cholerae* O395Vibrio (9 proteins) PHA0454 | DNA ligase | YP_002819900 |
| b. Viruses | | |
| Enterobacteria phage 13aT7-like viruses (16 proteins) | ATP-dependent DNA ligase | YP_002003941 |
| Enterobacteria phage BA14T7-like viruses (16 proteins) | ATP-dependent DNA ligase | YP_002003458 |
| Enterobacteria phage EcoDS1T7-like viruses (16 proteins) | ATP-dependent DNA ligase | YP_002003747 |
| Enterobacteria phage K1FT7-like viruses (16 proteins) | ATP-dependent DNA ligase | YP_338096 |
| Enterobacteria phage T3T7-like viruses (16 proteins) | ATP-dependent DNA ligase | NP_523305 |
| Enterobacteria phage T7T7-like viruses (16 proteins) | ATP-dependent DNA ligase | NP_041963 |
| *Klebsiella* phage K11T7-like viruses (16 proteins) | ATP-dependent DNA ligase | YP_002003797 |
| *Kluyvera* phage Kvp1T7-like viruses (16 proteins) | DNA ligase | YP_002308390 |
| *Morganella* phage MmP1T7-like viruses (16 proteins) | ATP-dependent DNA ligase | YP_002048633 |

TABLE 1A-continued

| Organism | Protein name | Accession |
| --- | --- | --- |
| *Pseudomonas* phage gh-1T7-like viruses (16 proteins) | ATP-dependent DNA ligase | NP_813751 |
| *Salmonella* phage phiSG-JL2T7-like viruses (16 proteins) | ATP-dependent DNA ligase | YP_001949754 |
| Vibriophage VP4T7-like viruses (16 proteins) | ATP-dependent DNA ligase | YP_249578 |
| *Yersinia pestis* phage phiA1122T7-like viruses (16 proteins) | ATP-dependent DNA ligase | NP_848267 |
| *Yersinia* phage BerlinT7-like viruses (16 proteins) | ATP-dependent DNA ligase | YP_918989 |
| *Yersinia* phage Yepe2T7-like viruses (16 proteins) | ATP-dependent DNA ligase | YP_002003318 |
| *Yersinia* phage phiYeO3-12T7-like viruses (16 proteins) | ATP-dependent DNA ligase | NP_052075 |
| Enterobacteria phage LKA1phiKMV-like viruses (7 proteins) | ATP-dependent DNA ligase | YP_001522868 |
| Enterobacteria phage phiKMVphiKMV-like viruses (7 proteins) | ATP-dependent DNA ligase | NP_877456 |
| *Pseudomonas* phage LKD16phiKMV-like viruses (7 proteins) | ATP-dependent DNA ligase | YP_001522807 |
| *Pseudomonas* phage LUZ19phiKMV-like viruses (7 proteins) | ATP-dependent DNA ligase | YP_001671961 |
| *Pseudomonas* phage PT2phiKMV-like viruses (7 proteins) | ATP-dependent DNA ligase | YP_002117800 |
| *Pseudomonas* phage PT5phiKMV-like viruses (7 proteins) | ATP-dependent DNA ligase | YP_002117741 |
| *Pseudomonas* phage phikF77phiKMV-like viruses (7 proteins) | ATP-dependent DNA ligase | YP_002727838 |
| CLSZ2445448 a. Eukaryota | | |
| *Paramecium tetraurelia* strain d4-2Paramecium (5 proteins) | DNA ligase | XP_001347270 |
| *Paramecium tetraurelia* strain d4-2Paramecium (5 proteins) | hypothetical protein | XP_001422985 |
| *Paramecium tetraurelia* strain d4-2Paramecium (5 proteins) | hypothetical protein | XP_001431968 |
| *Paramecium tetraurelia* strain d4-2Paramecium (5 proteins) | hypothetical protein | XP_001435874 |
| *Paramecium tetraurelia* strain d4-2Paramecium (5 proteins) | hypothetical protein | XP_001460273 |
| *Tetrahymena thermophila*Tetrahymena (1 proteins) | ATP dependent DNA ligase | XP_001011861 |
| CLSP2344013 b. Viruses | | |
| Enterobacteria phage Felix 01unclassified Myoviridae (4 proteins) | Putative DNA ligase | NP_944942 |
| Enterobacteria phage WV8unclassified Myoviridae (4 proteins) | hypothetical protein | YP_002922879 |
| *Erwinia* phage phiEa21-4unclassified Myoviridae (4 proteins) | putative DNA ligase | YP_002456101 |
| *Escherichia* phage rv5unclassified Myoviridae (4 proteins) | ATP-dependent DNA ligase | YP_002003586 |
| PRK07636 J. Firmicutes | | |
| *Bacillus clausii* KSM-K16Bacillus | ATP-dependent DNA ligase | YP_176304 |
| *Bacillus subtilis* subsp. *subtilis* str. 168Bacillus | ATP-dependent DNA ligase | NP_389932 |
| *Bacillus licheniformis* ATCC 14580Bacillus | ATP-dependent DNA ligase | YP_078721 |
| *Bacillus licheniformis* ATCC 14580Bacillus | ATP-dependent DNA ligase | YP_091132 |
| *Geobacillus* sp. Y412MC10Geobacillus | ATP dependent DNA ligase | YP_003240778 |
| *Paenibacillus* sp. JDR-2Paenibacillus | ATP dependent DNA ligase | YP_003009892 |
| CLSK2551528 J. Firmicutes | | |
| *Geobacillus* sp. Y412MC10Geobacillus (1 proteins) | ATP dependent DNA ligase | YP_003245332 |
| *Paenibacillus* sp. JDR-2Paenibacillus (1 proteins) | ATP dependent DNA ligase | YP_003013681 |
| CLSK2532515 B. Acidobacteria | Protein name | Accession |
| *Candidatus Solibacter usitatus* Ellin6076Candidatus Solibacter (1 proteins) | ATP dependent DNA ligase | YP_829024 |

TABLE 1A-continued

| Organism | Protein name | Accession |
|---|---|---|
| E. Bacteroides/Chlorobi | | |
| Flavobacteriaceae bacterium 3519-10unclassified Flavobacteriaceae (1 proteins) CLSK2470953 | ATP-dependent DNA ligase | YP_003095681 |
| C. Actinobacteria | | |
| *Arthrobacter chlorophenolicus* A6 (plasmid)*Arthrobacter* (2 proteins) | ATP dependent DNA ligase | YP_002478051 |
| *Arthrobacter chlorophenolicus* A6 (plasmid)*Arthrobacter* (2 proteins) | ATP dependent DNA ligase | YP_002478427 |
| *Nocardioides* sp. JS614Nocardioides (1 proteins) CLSK2469924 | ATP dependent DNA ligase | YP_923463 |
| J. Firmicutes | | |
| *Alicyclobacillus acidocaldarius* subsp. *acidocaldarius* DSM 446Alicyclobacillus (1 proteins) | ATP dependent DNA ligase | YP_003185050 |
| *Brevibacillus brevis* NBRC 100599Brevibacillus (1 proteins) CLSK2340991 | putative ATP-dependent DNA ligase | YP_002773127 |
| | Protein name | Accession |
| N. Alphaproteobacteria | | |
| *Phenylobacterium zucineum* HLK1 (plasmid)*Phenylobacterium* (2 proteins) | ATP dependent DNA ligase | YP_002128561 |
| *Phenylobacterium zucineum* HLK1 (plasmid)*Phenylobacterium* (2 proteins) CLSK2333706 | ATP-dependent DNA ligase | YP_002128631 |
| J. Firmicutes | | |
| *Candidatus Desulforudis audaxviator* MP104CCandidatus Desulforudis (1 proteins) | ATP dependent DNA ligase | YP_001716762 |
| *Natranaerobius thermophilus* JW/NM-WN-LFNatranaerobius (1 proteins) CLSK2303611 | ATP dependent DNA ligase | YP_001916325 |
| C. Actinobacteria | | |
| *Streptomyces coelicolor* A3(2)*Streptomyces* (2 proteins) | ATP-dependent DNA ligase | NP_631399 |
| *Streptomyces griseus* subsp. *griseus* NBRC 13350Streptomyces (2 proteins) CLSK962101 | putative ATP-dependent DNA ligase | YP_001828202 |
| C. Actinobacteria | | |
| *Nocardioides* sp. JS614Nocardioides (1 proteins) | ATP dependent DNA ligase | YP_922436 |
| *Salinispora arenicola* CNS-205Salinispora (2 proteins) | DNA polymerase LigD ligase region | YP_001539124 |
| *Salinispora tropica* CNB-440Salinispora (2 proteins) CLSK915249 | ATP dependent DNA ligase | YP_001160776 |
| C. Actinobacteria See CLSK2303611 above | | |
| *Streptomyces avermitilis* MA-4680 (plasmid)*Streptomyces* (2 proteins) | putative ATP-dependint DNA ligase | NP_828839 |
| *Streptomyces* sp. HK1 (plasmid)*Streptomyces* (2 proteins) CLSK899085 | putative ATP-dependent DNA ligase | YP_001661618 |
| O. Betaproteobacteria | | |
| *Burkholderia cenocepacia* HI2424 (plasmid)*Burkholderia* (3 proteins) | ATP dependent DNA ligase | YP_840498 |
| *Burkholderia cenocepacia* J2315 (plasmid)*Burkholderia* (3 proteins) | putative ligase | YP_002235530 |
| *Burkholderia multivorans* ATCC 17616 (plasmid)*Burkholderia* (3 proteins) | DNA polymerase LigD ligase subunit | YP_001573706 |
| R. Gammaproteobacteria | | |
| *Pseudomonas putida* (plasmid)*Pseudomonas* (1 proteins) CLSK862724 | putative ligase | NP_542805 |
| A. Archaea | | |
| *Archaeoglobus fulgidus* DSM 4304Archaeoglobus (1 proteins) | DNA ligase, putative | NP_070553 |

TABLE 1A-continued

| Organism | Protein name | Accession |
|---|---|---|
| J. Firmicutes | | |
| *Desulfotomaculum reducens* MI-1Desulfotomaculum (1 proteins) | ATP dependent DNA ligase | YP_001113345 |
| *Moorella thermoacetica* ATCC 39073Moorella (1 proteins) | ATP dependent DNA ligase, central | YP_430340 |
| *Pelotomaculum thermopropionicum* SIPelotomaculum (1 proteins) | ATP-dependent DNA ligase | YP_001211793 |
| *Thermoanaerobacter pseudethanolicus* ATCC 33223Thermoanaerobacter (2 proteins) | ATP dependent DNA ligase | YP_001664477 |
| *Thermoanaerobacter* sp. X514Thermoanaerobacter (2 proteins) CLSK820690 | ATP dependent DNA ligase | YP_001662589 |
| A. Archaea | | |
| uncultured methanogenic archaeon RC-Ienvironmental samples (1 proteins) | ATP-dependent DNA ligase | YP_686457 |
| C. Actinobacteria | | |
| *Mycobacterium avium* 104Mycobacterium (2 proteins) | DNA polymerase LigD ligase subunit | YP_882332 |
| *Mycobacterium avium* subsp. *paratuberculosis* K-10Mycobacterium (2 proteins) | hypothetical protein | NP_960263 |
| *Saccharopolyspora erythraea* NRRL 2338Saccharopolyspora (1 proteins) | DNA ligase, ATP-dependent | YP_001107793 |
| N. Alphaproteobacteria | | |
| *Bradyrhizobium japonicum* USDA 110Bradyrhizobium (2 proteins) | DNA ligase | NP_774671 |
| *Bradyrhizobium* sp. BTAi1Bradyrhizobium (2 proteins) CLSK808255 | putative ATP-dependent DNA ligase | YP_001243518 |
| N. Alphaproteobacteria | | |
| *Sinorhizobium medicae* WSM419Sinorhizobium (2 proteins) | DNA polymerase LigD ligase region | YP_001326990 |
| *Sinorhizobium meliloti* 1021 (plasmid)*Sinorhizobium* (2 proteins) CLSK806855 | putative ATP-dependent DNA ligase protein | NP_437750 |
| N. Alphaproteobacteria | | |
| *Agrobacterium tumefaciens* str. C58 (plasmid)*Agrobacterium* (3 proteins) | ATP-dependent DNA ligase | NP_395985 |
| *Agrobacterium tumefaciens* str. C58 (plasmid)*Agrobacterium* (3 proteins) | ATP-dependent DNA ligase | NP_396032 |
| *Agrobacterium tumefaciens* str. C58 (plasmid)*Agrobacterium* (3 proteins) | ATP-dependent DNA ligase | NP_396609 |
| *Rhizobium etli* CFN 42 (plasmid)*Rhizobium* (10 proteins) | putative DNA ligase (ATP) protein | YP_472413 |
| *Rhizobium etli* CIAT 652Rhizobium (10 proteins) | probable ATP-dependent DNA ligase protein | YP_001977317 |
| *Rhizobium etli* CIAT 652 (plasmid)*Rhizobium* (10 proteins) | putative ATP-dependent DNA ligase protein | YP_001985803 |
| *Rhizobium leguminosarum* bv. *trifolii* WSM1325 (plasmid)*Rhizobium* (10 proteins) | DNA polymerase LigD, ligase domain protein | YP_002973496 |
| *Rhizobium leguminosarum* bv. *trifolii* WSM1325 (plasmid)*Rhizobium* (10 proteins) | DNA polymerase LigD, ligase domain protein | YP_002984974 |
| *Rhizobium leguminosarum* bv. *trifolii* WSM1325 (plasmid)*Rhizobium* (10 proteins) | DNA polymerase LigD, ligase domain protein | YP_002984992 |
| *Rhizobium leguminosarum* bv. *trifolii* WSM2304Rhizobium (10 proteins) | DNA polymerase LigD, ligase domain protein | YP_002281897 |
| *Rhizobium leguminosarum* bv. *trifolii* WSM2304 (plasmid)*Rhizobium* (10 proteins) | DNA polymerase LigD, ligase domain protein | YP_002278005 |
| *Rhizobium leguminosarum* bv. *viciae* 3841 (plasmid)*Rhizobium* (10 proteins) | putative DNA ligase | YP_764723 |
| *Rhizobium leguminosarum* bv. *viciae* 3841 (plasmid)*Rhizobium* (10 proteins) | putative DNA ligase | YP_771149 |
| *Sinorhizobium meliloti* (plasmid)*Sinorhizobium* (2 proteins) | putative ATP-dependent DNA ligase | YP_001965531 |
| *Sinorhizobium meliloti* 1021 (plasmid)*Sinorhizobium* (2 proteins) CLSK762775 | ATP-dependent DNA ligase | NP_435470 |
| N. Alphaproteobacteria | | |
| *Rhodococcus jostii* RHA1 (plasmid)*Rhodococcus* (2 proteins) | ATP-dependent DNA ligase | YP_708952 |
| *Rhodococcus opacus* B4 | putative ATP-dependent | YP_002776886 |

TABLE 1A-continued

| Organism | Protein name | Accession |
|---|---|---|
| (plasmid)*Rhodococcus* (2 proteins) CLSK761995 | DNA ligase | |
| N. Alphaproteobacteria | | |
| *Nitrobacter hamburgensis* X14Nitrobacter (1 proteins) | ATP dependent DNA ligase | YP_579015 |
| *Rhodopseudomonas palustris* BisB5Rhodopseudomonas (2 proteins) | ATP dependent DNA ligase | YP_569297 |
| *Rhodopseudomonas palustris* TIE-1Rhodopseudomonas (2 proteins) CLSK523944 | DNA polymerase LigD, ligase domain protein | YP_001991309 |
| R. Gammaproteobacteria | | |
| *Pseudomonas fluorescens* (plasmid)*Pseudomonas* (3 proteins) | putative ATP-dependent DNA ligase | YP_002887417 |
| *Pseudomonas putida* (plasmid)*Pseudomonas* (3 proteins) | putative ligase fragment | NP_863069 |
| *Pseudomonas* sp. ND6 (plasmid)*Pseudomonas* (3 proteins) CLSK390680 | ATP-dependent DNA ligase | NP_943185 |
| R. Gammaproteobacteria | | |
| *Mesorhizobium loti* MAFF303099Mesorhizobium (3 proteins) | ATP-dependent DNA ligase | NP_108227 |
| *Mesorhizobium loti* MAFF303099Mesorhizobium (3 proteins) | hypothetical protein | NP_108282 |
| *Mesorhizobium loti* MAFF303099 (plasmid)*Mesorhizobium* (3 proteins) | DNA ligase-like protein | NP_109396 |

A subset of ligases of interest is in Table 1B below.

TABLE 1B

| Organism | Protein name | Accession |
|---|---|---|
| PRK08224 | | |
| B. Acidobacteria | | |
| Bacteria; Fibrobacteres/Acidobacteria group; Acidobacteria; unclassifed Acidobacteria; *Candidatus Koribacter*; *Candidatus Koribacter versatilis* *Candidatus Solibacter usitatus* Ellin6076Candidatus Solibacter (1 proteins) | ATP-Dependent DNA Ligase | YP_826317 |
| C. Actinobacteria | | |
| Bacteria; Actinobacteria; Actinobacteria (class); Actinobacteridae; Actinomycetales; Corynebacterineae; Mycobacteriaceae; *Mycobacterium*; *Mycobacterium marinum* | | |
| *Mycobacterium gilvum* PYR-GCKMycobacterium (26 proteins) | ATP-Dependent DNA Ligase | YP_001132524 |
| *Mycobacterium vanbaalenii* PYR-1Mycobacterium (26 proteins) | ATP-Dependent DNA Ligase | YP_956315 |
| *Mycobacterium* sp. MCSMycobacterium (26 proteins) | ATP-Dependent DNA Ligase | YP_642076 |
| F. Chlamydiae/Verrucomicrobia | | |
| Bacteria; Chlamydiae/Verrucomicrobia group; Verrucomicrobia; Opitutae; Opitutales; Opitutaceae; *Opitutus*; *Opitutus terrae* *Opitutus terrae* PB90-1Opitutus (1 proteins) | ATP-Dependent DNA Ligase | YP_001821013 |
| PRK09125 | | |
| O. Betaproteobacteria | | |
| *Neisseria meningitidis* Z2491Neisseria (7 proteins) | DNA ligase | YP_002341892 |
| *Thiobacillus denitrificans* ATCC 25259Thiobacillus (1 proteins) | DNA ligase | YP_314570 |
| *Variovorax paradoxus* S110Variovorax (1 proteins) | DNA ligase | YP_002944627 |
| *Verminephrobacter eiseniae* EF01-2Verminephrobacter (1 proteins) | DNA ligase | YP_998235 |
| | — | — |
| P. Deltaproteobacteria | | |
| *Desulfobacterium autotrophicum* HRM2Desulfobacterium (1 proteins) | LigA2 | YP_002604477 |

TABLE 1B-continued

| Organism | Protein name | Accession |
|---|---|---|
| *Myxococcus xanthus* DK 1622Myxococcus (1 proteins) | DNA ligase | YP_628883 |
| Q. Epsilonproteobacteria | — | — |
| *Campylobacter jejuni* subsp. *jejuni* NCTC 11168Campylobacter (10 proteins) | ATP-dependent DNA ligase | YP_002345037 |
| *Sulfurimonas denitrificans* DSM 1251Sulfurimonas (1 proteins) | DNA ligase | YP_393098 |
| R. Gammaproteobacteria | — | — |
| *Aggregatibacter aphrophilus* NJ8700Aggregatibacter (2 proteins) | ATP-dependent DNA ligase | YP_003007537 |
| *Haemophilus influenzae* PittEEHaemophilus (3 proteins) | ATP-dependent DNA ligase | YP_001290961 |
| *Shewanella baltica* OS195Shewanella (18 proteins) | ATP-dependent DNA ligase | YP_001554317 |
| *Shewanella loihica* PV-4Shewanella (18 proteins) | ATP-dependent DNA ligase | YP_001093713 |
| *Vibrio cholerae* M66-2Vibrio (9 proteins) | DNA ligase | YP_002810248 |
| PHA0454 b. Viruses | — | — |
| Viruses; dsDNA viruses, no RNA stage; Caudovirales; Podoviridae; Autographivirinae; phiKMV-like viruses *Pseudomonas* phage LKD16phiKMV-like viruses (7 proteins) | ATP-dependent DNA ligase | YP_001522807 |
| CLSZ2445448 a. Eukaryota | | |
| Eukaryota; Alveolata; Ciliophora; Intramacronucleata; Oligohymenophorea; Peniculida; Parameciidae; *Paramecium*; *Paramecium tetraurelia* *Paramecium tetraurelia* strain d4-2Paramecium (5 proteins) | DNA ligase | XP_001347270 |
| PRK07636 J. Firmicutes | | |
| Bacteria; Firmicutes; Bacilli; Bacillales; Bacillaceae; *Bacillus*; *Bacillus clausii* *Bacillus subtilis* subsp. *subtilis* str. 168Bacillus | ATP-dependent DNA ligase | NP_389932 |
| Bacteria; Firmicutes; Bacilli; Bacillales; Bacillaceae; *Geobacillus* *Geobacillus* sp. Y412MC10Geobacillus | ATP dependent DNA ligase | YP_003240778 |
| CLSK2551528 J. Firmicutes | | |
| Bacteria; Firmicutes; Bacilli; Bacillales; Bacillaceae; *Geobacillus* *Geobacillus* sp. Y412MC10Geobacillus (1 proteins) | ATP dependent DNA ligase | YP_003245332 |
| CLSK2470953 C. Actinobacteria | — | — |
| Bacteria; Actinobacteria; Actinobacteria (class); Actinobacteridae; Actinomycetales; Micrococcineae; Micrococcaceae; *Arthrobacter*; *Arthrobacter chlorophenolicus* *Arthrobacter chlorophenolicus* A6 (plasmid)*Arthrobacter* (2 proteins) | ATP dependent DNA ligase | YP_002478427 |
| CLSK2469924 J. Firmicutes | | |
| Bacteria; Firmicutes; Bacilli; Bacillales; Alicyclobacillaceae; *Alicyclobacillus*; *Alicyclobacillus acidocaldarius*; *Alicyclobacillus acidocaldarius* subsp. *acidocaldarius* *Alicyclobacillus acidocaldarius* subsp. *acidocaldarius* DSM 446Alicyclobacillus | ATP dependent DNA ligase | YP_003185050 |
| CLSK2340991 N. Alphaproteobacteria | | |
| Bacteria; Proteobacteria; Alphaproteobacteria; Caulobacterales; Caulobacteraceae; *Phenylobacterium*; *Phenylobacterium zucineum* | | |

TABLE 1B-continued

| Organism | Protein name | Accession |
|---|---|---|
| *Phenylobacterium zucineum* HLK1 (plasmid)*Phenylobacterium* (2 proteins) | ATP-dependent DNA ligase | YP_002128631 |
| CLSK2333706 J. Firmicutes | — | — |
| Bacteria; Firmicutes; Clostridia; Clostridiales; Peptococcaceae; *Candidatus Desulforudis*; Candidatus Desulforudis audaxviator *Candidatus Desulforudis audaxviator* MP104CCandidatus Desulforudis (1 proteins) | ATP dependent DNA ligase | YP_001716762 |
| CLSK962101 C. Actinobacteria | — | — |
| Bacteria; Actinobacteria; Actinobacteria (class); Actinobacteridae; Actinomycetales; Micromonosporineae; Micromonosporaceae; *Salinispora*; *Salinispora arenicola* | | |
| *Salinispora arenicola* CNS-205Salinispora (2 proteins) | DNA polymerase LigD ligase region | YP_001539124 |
| *Salinispora tropica* CNB-440Salinispora (2 proteins) | ATP dependent DNA ligase | YP_001160776 |
| CLSK915249 C. Actinobacteria See CLSK2303611 above | — | — |
| Bacteria; Actinobacteria; Actinobacteria (class); Actinobacteridae; Actinomycetales; Streptomycineae; Streptomycetaceae; *Streptomyces*; *Streptomyces coelicolor* | | |
| *Streptomyces avermitilis* MA-4680 (plasmid)*Streptomyces* (2 proteins) | putative ATP-dependint DNA ligase | NP_828839 |
| *Streptomyces* sp. HK1 (plasmid)*Streptomyces* (2 proteins) | putative ATP-dependent DNA ligase | YP_001661618 |
| CLSK862724 A. Archaea | | |
| Archaea; Euryarchaeota; Archaeoglobi; Archaeoglobales; Archaeoglobaceae; *Archaeoglobus*; *Archaeoglobus fulgidus* | | |
| *Archaeoglobus fulgidus* DSM 4304Archaeoglobus (1 proteins) | DNA ligase, putative | NP_070553 |
| J. Firmicutes | | |
| *Pelotomaculum thermopropionicum* SIPelotomaculum (1 proteins) | ATP-dependent DNA ligase | YP_001211793 |
| *Thermoanaerobacter pseudethanolicus* ATCC 33223Thermoanaerobacter (2 proteins) | ATP dependent DNA ligase | YP_001664477 |
| CLSK820690 A. Archaea | | |
| Archaea; Euryarchaeota; environmental samples uncultured methanogenic archaeon RC-Ienvironmental samples (1 proteins) | ATP-dependent DNA ligase | YP_686457 |
| N. Alphaproteobacteria | | |
| Bacteria; Proteobacteria; Alphaproteobacteria; Rhizobiales; Bradyrhizobiaceae; *Bradyrhizobium*; *Bradyrhizobium japonicum* | | |
| *Bradyrhizobium japonicum* USDA 110Bradyrhizobium (2 proteins) | DNA ligase | NP_774671 |
| *Bradyrhizobium* sp. BTAi1Bradyrhizobium (2 proteins) | putative ATP-dependent DNA ligase | YP_001243518 |
| CLSK808255 N. Alphaproteobacteria | | |
| Bacteria; Proteobacteria; Alphaproteobacteria; Rhizobiales; Rhizobiaceae; *Sinorhizobium/Ensifer* group; *Sinorhizobium*; *Sinorhizobium medicae* | | |
| *Sinorhizobium medicae* WSM419Sinorhizobium (2 proteins) | DNA polymerase LigD ligase region | YP_001326990 |
| *Sinorhizobium meliloti* 1021 (plasmid)*Sinorhizobium* (2 proteins) | putative ATP-dependent DNA ligase protein | NP_437750 |
| CLSK806855 N. Alphaproteobacteria | | |
| Bacteria; Proteobacteria; Alphaproteobacteria; Rhizobiales; Rhizobiaceae; *Rhizobium/Agrobacterium* group; *Agrobacterium*; *Agrobacterium tumefaciens* | | |

TABLE 1B-continued

| Organism | Protein name | Accession |
|---|---|---|
| *Agrobacterium tumefaciens* str. C58 (plasmid)*Agrobacterium* (3 proteins) | ATP-dependent DNA ligase | NP_396032 |
| *Rhizobium leguminosarum* bv. *trifolii* WSM1325 (plasmid)*Rhizobium* (10 proteins) | DNA polymerase LigD, ligase domain protein | YP_002973496 |
| *Rhizobium leguminosarum* bv. *trifolii* WSM2304 (plasmid)*Rhizobium* (10 proteins) CLSK390680 N. Alphaproteobacteria | DNA polymerase LigD, ligase domain protein | YP_002278005 |
| Bacteria; Proteobacteria; Alphaproteobacteria; Rhizobiales; Phyllobacteriaceae; *Mesorhizobium*; *Mesorhizobium loti* *Mesorhizobium loti* MAFF303099*Mesorhizobium* (3 proteins) | hypothetical protein | NP_108282 |

Some exemplary ligases are identified and their GI or accession numbers are provided in Table 1C below:

TABLE 1C

```
CV DNA Ligase, GenBank ID AAC96909.1, from Paramecium
bursaria Chlorella virus 1:
MAITKPLLAATLENIEDVQFPCLATPKIDGIRSVKQTQMLSRTFKPIRNSVMNRLL
TELLPEGSDGEISIEGATFQDTTSAVMTGHKMYNAKFSYYWFDYVTDDPLKKYIDR
VEDMKNYITVHPHILEHAQVKIIPLIPVEINNITELLQYERDVLSKGFEGVMIRKP
DGKYKFGRSTLKEGILLKMKQFKDAEATIISMTALFKNTNTKTKDNFGYSKRSTHK
SGKVEEDVMGSIEVDYDGVVFSIGTGFDADQRRDFWQNKESYIGKMVKFKYFEMGS
KDCPRFPVFIGIRHEEDR MnM DNA Ligase, GenBank ID YP_333052.1, from Burkholderia
pseudomallei 1710b (equivalent sequence to ABA50091)
MSGVPYGFKPNLAATLTKPELIKFPVWASPKIDGIRCVFFGGVAYSRSLKPIPNP
VVQEFAKAYANLLEGLDGELTVGSPTDANCMQNSMAVMSKAAAPDFTFHVFDWFH
PAQAHIEFWQRSDVVEDRIVQFYDRYPEVDIRAAPQVLCTSLAHLDTNEARWLAD
GYEGMMIRDHCGRYKFGRSTEREGGLVKVKRFTDAEAIVIGFEEEMHNANEAKRD
ATGRTERSTSKAGLHGKGTLGALVVKNERGIVFNIGTGFTAAQRADYWANHPSLF
GKMVKFKHFDHGTVDAPRHPVFIGFRHPEDM Hin DNA Ligase, GenBank ID P44121, from Haemophilus influenza
MKFYRTLLLFFASSFAFANSDLMLLHTYNNQPIEGWVMSEKLDGVRGYWNGKQLL
TRQGQRLSPPAYFIKDFPPFAIDGELFSERNHFEEISTITKSFKGDGWEKLKLYV
FDVPDAEGNLFERLAKLKAHLLEHPTTYIEIIEQIPVKDKTHLYQFLAQVENLQG
EGVVVRNPNAPYERKRSSQILKLKTARGEECTVIAHHKGKGQFENVMGALTCKNH
RGEFKIGSGFNLNERENPPPIGSVITYKYRGITNSGKPRFATYWREKK DLX DNA Ligase, artificial ligase derived from Hin DNA
ligase from Haemophilus influenza:
MKFYRTLLLFFASSFAFANSDLMLLHTYNNQPIEGWVMSEKLDGVRGYWNGKQLL
TRQGQRLSPPAYFIKDFPPFAIDGELFSERNHFEEISSITKSFKGDGWEKLKLYV
FDVPDAEGNLFERLAKLKAHLLEHPTTYIEIIEQIPVKDKTHLYQFLAQVENLQG
EGVVVRNPNAPYERKRSSQILKLKTARGEECTVIAHHKGKGQFENVMGALTCKNH
RGEFKIGSGFNLNERENPPPIGSVITYKYRGITNSGKPRFATYWREKK DLXd DNA Ligase, artificial ligase derived from Hin D
ligase from Haemophilus influenza:
MKFYRTLLLFFASSFAFANSDLMLLHTYNNQPIEGWVMSEKLDGVRGYWNGKQLL
TRQGQRLSPPAYFIKDFPPFAIDGELFSERNHFEEISSITKSFKGDGWEKLKLYV
FDVPDAEGNLFERLAKLKAHLLEHPTTYIEIIEQIPVKDKTHLYQFLAQVENLQG
EGVVVRNPNAPYERKRSSQILKLKTARDEECTVIAHHKGKGQFENVMGALTCKNH
RGEFKIGSGFNLNERENPPPIGSVITYKYRGITNSGKPRFATYWREKK DLXd2 DNA Ligase (Gammaproteobacteria, Haemophilus influenza)
(modified)
MLLHTYNNQPIEGWVMSEKLDGVRGYWNGKQLLTRQGQRLSPPAYFIKDFPPFAID
GELFSERNHFEEISSITKSFKGDGWEKLKLYVFDVPDAEGNLFERLAKLKAHLLEHPT
TYIEIIEQIPVKDKTHLYQFLAQVENLQGEGVVVRNPNAPYERKRSSQILKLKTARDE
ECTVIAHHKGKGQFENVMGALTCKNHRGEFKIGSGFNLNERENPPPIGSVITYKYRGI
TNSGKPRFATYWREKK
```

The SFL is in one aspect an enzyme that can mediate the formation of a covalent bond between two polynucleotide termini, e.g., a 3'-OH terminus and a 5'-PO4 terminus are joined together to form a phosphodiester bond. In some instances, DNA ligation entails any one or more of three sequential nucleotidyl transfer steps, discussed below. All three chemical steps depend on a divalent cation cofactor. In one aspect, the SFL is an ATP-dependent ligase or a $NAD^+$-dependent ligase.

Optionally, the SFL is *Chlorella* virus DNA ligase (ChV-Lig). Ho, et al., J Virol, 71(3):1931-19374 (1997) or functional fragment or variant thereof. For example the SFL can comprise any one or more domains characteristic of a ligase, e.g., an N-terminal nucleotidyltransferase (NTase) domain and/or a C-terminal OB domain. The OB domain optionally comprises a five-stranded antiparallel beta-barrel plus an alpha-helix. Within the NTase domain is an adenylate-binding pocket composed of the six peptide motifs that define the covalent NTase enzyme family of polynucleotide ligases. Optionally, the NTase domain can comprise any one or more of the ligase amino acid motifs I, Ia, III, IIIa, IV, V, and VI preferably all six motifs. Motif I (e.g., K×DG×R or a "KXDG" motif) optionally contains a lysine. Exemplary sequences for each motif in CV ligase are ATPKIDGIR (motif I), SRT (motif Ia), EGSDGEIS (motif III), YWFDY (motif IIIa), EGVMIR (motif IV), LLKMK (motif V). Motif 1 preferably contains a lysine residue. Other examples of motif I include CELKLDGLA, VEHKVDGLS, CEPKLDGLA, CELKLDGVA, AEIKYDGVR, CEYKYDGQR, VDYKYDGER, FEIKYDGAR, FEGKWDGYR, AREKIHGTN, ACEKVHGTN, ILTKEDGSL, and VEEKVDGYN. Examples of motif Ia include TRG, SRT, SRR, SRN, SRS, KRT, KRS, SKG and TRG. Examples of motif III include LEVRGEVF, VEVRGECY, LEVRGEVY, LEARGEAF, FMLDGELM, EGSDGEIS, FILDTEAV, FIIEGEIV, AIVEGELV, VVLDGEAV, YQVFGEFA, LVLNGELF, FTANFEFV and LILVGEMA. Examples of motif IIIa include FCYGV, FLYTV, TFYAL, ICHGL, NAYGI, FVYGL, KLYAI, YWFDY, YAFDI, FLFDL, NLFDV, WAFDL, YVFDI, FAFDI, ILLNA, AND FLFDV. Examples of motif IV include DGVVIK, DGIVIK, DGVVVK, DGTVLK, EGLIVK, EGVMIR, EGLMVK, EGVMVK, EGLMAK, EGVIAK, EGYVLK, EGVVIR, EGYVAV, and EGIIMK. Examples of motif V include AVAFK, AIAYK, ALAYK, AIAYK, WWKMK, LLKMK, WLKLK, WIKLK, WLKIK, WVKDK, AIKCK, IIKLR, HFKIK and IVKYV. The SFL optionally comprises all six motifs. Optionally all six motifs are found together in a naturally-occurring ligase, such as a SFL identified herein. Optionally, the SFL is not an RNA-capping enzyme.

The ligase optionally comprises any functional portion of a SFL. The ligase can be homologous to a SFL or any functional portion thereof, for example more than 75%, 85%, 90%, 95% or 99% homologous at the amino acid level.

Optionally, any of the ligation methods described herein is performed by an SFL that is not CV ligase or a functional fragment or derivative thereof. Optionally, the SFL is not T4 DNA ligase or functional fragment or variant thereof. Optionally, the SFL is less than 70%, 80% or 90% identical to T4 DNA ligase. In some examples, the SFL is not a ligase that was known by effective filing date of this application to efficiently ligate oligonucleotides shorter than 6 nucleotides in length. In some examples, the SFL is not a ligase that was known by Jan. 11, 2011, to efficiently ligate oligonucleotides shorter than 6 nucleotides in length.

In a typical assay, a probe that is 2, 3, 4, 5 or 6 nucleotides in length is ligated in template-dependent manner to a primer using an SFL. Optionally, the 3' end of the probe is ligated to the 5' end of the primer, or vice versa. Optionally, the SFL is CV ligase. The efficiency of ligation is for example more than 5%, 10%, 20%, 30%, or 50%. In other instances a probe that is 6, 7, 8, 9, 10, 11 or 12 nucleotides in length is ligated in template-dependent manner to a primer using an SFL. Optionally, the 5' end of the probe is ligated to the 3' end of the primer, or vice versa. Optionally, the SFL is CV ligase. The efficiency of ligation is for example more than 80%, 90% or 95%.

In any ligation described herein, ligation product is optionally detected. Ligation can be detected by any known method or method described herein. For example the primer and/or template can be immobilized on a support and the probe labeled. The label on the ligated immobilized probe can be detected after non-ligated probe has been washed away. In other embodiments any one or more of the probe, primer or template is labeled. Any one or more of these reagents can optionally be immobilized.

In any ligation herein, the ligation can be repeated for a desired number of cycles, for example any reagent that has been subjected to a first ligation cycle is used as a reagent in a next ligation cycle. For example the primer, probe or template of a first ligation cycle can be used as primer, probe or template in a next ligation cycle. In some embodiments (e.g., ligation sequencing) the primer of a first cycle is used as primer in the next cycle. In other instances, the primer of a first cycle can be used a probe or template in the next, the probe of a first cycle can be used as primer or template, or the template of a first cycle can be used as primer or probe the next.

The next cycle can be designed such that both ligated and unligated reagent of a first cycle can act as reagent in the next cycle. For example, the ligated and unligated primer of a first ligation cycle can be used as primer in the next cycle. Alternatively, the next cycle can be designed such that only a ligation product of the first cycle can act as a ligation reagent in the next cycle, and reagents that remain unligated in the first cycle will not act as reagents in the next cycle. In some examples, the unligated reagents of the previous cycle are "capped" or otherwise rendered unligatable before the next cycle of ligation is executed.

Any one or more ligases and/or ligation methods encompassed by the invention can optionally be used in one or more ligation assay formats, and/or are performed in the context of one or more specific ligation applications. Non-limiting examples of assay formats include: oligonucleotide ligation assay (OLA), a ligase chain reaction (LCR), a ligase detection reaction (LDR) and combination assays such as the OLA coupled with the polymerase chain reaction (PCR), e.g., OLA-PCR and PCR-OLA, the Combined Chain Reaction (CCR; a combination of PCR and LCR) and PCR-LDR (see, e.g., Landegren et al., Science 241:1077-80, 1988; Barany, Proc. Natl. Acad. Sci. 88:189-93, 1991; Grossman et al., Nucl. Acids Res. 22(21):4527-34, 1994; Bi and Stambrook, Nucl. Acids Res. 25(14):2949-51, 1997; Zirvi et al., Nucl. Acids Res., 27(24):e40, 1999; U.S. Pat. No. 4,988, 617; and PCT Publication Nos. WO 97/31256 and WO 01/92579. Non-limiting examples of specific applications include: amplification of template, detection and/or quantification of the presence of a particular nucleic acid, e.g., in a diagnostic sample, ligation sequencing, single nucleotide polymorphism (SNP) analysis, SNP genotyping, mutation detection, identification of single copy genes, detecting microsatellite repeat sequences, and DNA adduct mapping, among other things. See also Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15-3-29 (1982); and Namsaraev, U.S. patent publication 2004/0110213.

In an embodiment, the method of ligation comprises or consists of a proximity ligation assay (PLA). PLAs typically involve at least three steps. The first step is typically the binding of first and second probes (e.g., antibody probes) to a ligand (e.g., a protein of interest) such that the probes are in close proximity to another. Each of the probes typically contain an oligonucleotide. The oligonucleotides are brought into proximity to one another with the binding of the probes and, in the second step, are then ligated to one another (e.g., the ligation event). The ligated oligonucleotides may then be amplified and detected to determine the presence of the ligand with a sample (e.g., a biological sample).

An exemplary PLA assay comprises the steps of determining the presence or absence of a target protein in a sample, comprising (a) contacting the target protein with at least a first and second binding agent, each binding agent having binding specificity for the protein and being adjoined to at least one polynucleotide, (b) ligating the oligonucleotides on the first and second binding agent to one another using a ligase to produce a target nucleic acid and amplifying the target nucleic acid; (c) detecting whether amplified target nucleic acid is present or not, and (d) concluding that the target protein is present in the sample if a significant amount of amplified target nucleic acid is detected, and/or concluding that the target protein is absent from the sample if a significant amount of amplified target nucleic acid is not detected. Optionally, step (d) alternatively or additionally comprises measuring or otherwise assessing the amount of amplified target nucleic acid, and taking the amount of amplified nucleic acid as an indicator of the amount of target protein present in the sample.

In any methods described herein, polynucleotide ligation probes can be used for detection of a target nucleic acid. The ligation probe is optionally capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The oligonucleotide ligation assay (OLA) is a convenient, highly-stringent method that permits distinction among known DNA sequence variants (Landegren, 1988). Multiplex analysis of highly polymorphic loci is useful for identification of individuals, e.g., for paternity testing and in forensic science, organ transplant donor-receiver matching, genetic disease diagnosis, prognosis, and pre-natal counseling, and other genetic-based testing which depend on the discrimination of single-base differences at a multiplicity of loci (Delahunty, 1996). For example, different assays where two PNA-DNA chimeras, a wild-type (WT) sequence chimera and a mutant sequence chimera, bear different fluorescent dyes. Only when the mutant sequence is present in the target sample, will the mutant sequence chimera ligate to the adjacently annealed second probe (oligo) if the mutant base pair is at the ligation site.

a) Sequence Determination

In some embodiments, successive cycles of ligation can be performed, where the ligation product of a previous cycle is used as primer, probe and/or template in a succeeding cycle.

An exemplary use of such repetitive ligation is ligation sequencing. A template to be sequenced optionally contains a primer-binding region and polynucleotide region of unknown sequence. A primer with a ligatable terminus (e.g., a free 3' OH group or 5' phosphate group) is annealed to the primer binding region. An extension probe is hybridized to the template adjacently to the primer. The proximal nucleotide of the probe forms a complementary base pair with unknown nucleotide in the template. The extension probe is then ligated to the primer, optionally with an SFL, resulting in an extended duplex. Following ligation, the label attached to extension probe is optionally detected. The process is repeated for a desired number of cycles, using the ligation product of one cycle as the primer of the next cycle. Optionally, the extension probe has a non-ligatable distal terminus, and is then cleaved to provide a ligatable extended duplex.

In one example, the 3' terminus of the primer is ligated to the 5' terminus of the extension probe. The optional step of cleavage can be done for example at a phosphorothiolate linkage using $AgNO_3$ or another salt that provides $Ag^+$ ions, leaving a phosphate group at the 3' end of the extended duplex. Phosphatase treatment is used to generate an extendable probe terminus on the extended duplex.

In one-base encoding, the label corresponds to the identity of nucleotide X. Thus nucleotide Y is identified as the nucleotide complementary to nucleotide X. In other encodings, the label does not have a one-to-one correspondence with the identity of any particular nucleotide in the template.

Also provided are probe families for use in various ligation methods herein, e.g., sequencing. The probe families are optionally characterized in that each probe family comprises a plurality of labeled oligonucleotide probes of different sequence and, at each position in the sequence, a probe family comprises at least 2 probes having different bases at that position. Probes in each probe family comprise the same label. Preferably the probes comprise a scissile internucleoside linkage. The scissile linkage can be located anywhere in the probe. Preferably the probes have a moiety that is not extendable by ligase at one terminus. Preferably the probes are labeled at a position between the scissile linkage and the moiety that is not extendable by ligase, such that cleavage of the scissile linkage following ligation of a probe to an extendable probe terminus results in an unlabeled portion that is ligated to the extendable probe terminus and a labeled portion that is no longer attached to the unlabeled portion.

In multiple-base encodings, the probes in each probe family preferably comprise at least j nucleosides X, wherein j is at least 2, and wherein each X is at least 2-fold degenerate among the probes in the probe family. Probes in each probe family further comprise at least k nucleosides N, wherein k is at least 2, and wherein N represents any nucleoside. In general, j+k is equal to or less than 100, typically less than or equal to 30. Nucleosides X can be located anywhere in the probe. Nucleosides X need not be located at contiguous positions. Similarly nucleosides N need not be located at contiguous positions. In other words, nucleosides X and N can be interspersed. Nevertheless, nucleosides X can be considered to have a 5'→3' sequence, with the understanding that the nucleosides need not be contiguous. For example, nucleosides X in a probe of structure $X_A N X_G N N X_C N$ would be considered to have the sequence AGC. Similarly, nucleosides N can be considered to have a sequence.

Nucleosides X can be identical or different but are not independently selected, i.e., the identity of each X is constrained by the identity of one or more other nucleosides X in the probe. Thus in general only certain combinations of nucleosides X are present in any particular probe and within the probes in any particular probe family. In other words, in each probe, the sequences of nucleosides X can only represent a subset of all possible sequences of length j. Thus the identity of one or more nucleotides in X limits the possible identities for one or more of the other nucleosides.

Nucleosides N are preferably independently selected and can be A, G, C, or T (or, optionally, a degeneracy-reducing nucleoside). Preferably the sequence of nucleosides N represents all possible sequences of length k, except that one or more N may be a degeneracy-reducing nucleoside. The probes thus contain two portions, of which the portion consisting of nucleosides N is referred to as the unconstrained portion and the portion consisting of nucleosides X is referred to as the constrained portion. As described above, the portions need not be contiguous nucleotides. Probes that contain a constrained portion and an unconstrained portion are referred to herein as partially constrained probes. Preferably one or more nucleosides in the constrained portion is at the proximal end of the probes, i.e., at the end that contains the nucleoside that will be ligated to the extendable probe terminus, which can be either the 5' or 3' end of the oligonucleotide probe in different embodiments of the invention.

Since the constrained portion of any oligonucleotide probe can only have certain sequences, knowing the identity of one or more of the nucleosides in the constrained portion of a probe, either by itself, or optionally in combination with the identity of the label on the probe, provides information about one or more of the other nucleotides in the constrained portion. The information may or may not be sufficient to precisely identify one or more of the other nucleosides, but it will be sufficient to eliminate one or more possible nucleotide combinations and/or permutations in the constrained portion. Optionally, the information is not sufficient to eliminate any possible identity of any one individual nucleotide in the constrained portion. In certain preferred embodiments, knowing the identity of one nucleoside in the constrained portion of a probe is sufficient to precisely identify each of the other nucleosides in the constrained portion, i.e., to determine the identity and order of the nucleosides that comprise the constrained portion.

As in the one-base-encoding sequencing methods described above, the most proximal nucleoside in an extension probe that is complementary to the template is ligated to an extendable terminus of an initializing oligonucleotide (in the first cycle of extension, ligation, and detection) and to an extendable terminus of an extended oligonucleotide probe in subsequent cycles of extension, ligation, and detection. Detection of the associated label determines the name of the probe family to which the newly ligated probe belongs. Since each position in the constrained portion of the probe is at least 2-fold degenerate, the name of the probe family does not in itself identify any nucleotide in the constrained portion. However, since the sequence of the constrained portion is one of a subset of all possible sequences of length j, identifying the probe family does eliminate certain possibilities for the sequence of the constrained portion. The constrained portion of the probe constitutes its sequence determining portion. Therefore, eliminating one or more possibilities for the identity of one or more nucleosides in the constrained portion of the probe by identifying the probe family to which it belongs eliminates one or more possibilities for the identity of a nucleotide in the template to which the extension probe hybridizes. In preferred embodiments of the invention the partially constrained probes comprise a scissile linkage between any two nucleosides.

In certain embodiments the partially constrained probes have the general structure $(X)_j(N)_k$, in which X represents a nucleoside, $(X)_j$ is at least 2-fold degenerate at each position such that X can be any of at least 2 nucleosides having different base-pairing specificities, N represents any nucleoside, j is at least 2, k is between 1 and 100, and at least one N or X other than the X at the probe terminus comprises a detectable moiety. Preferably $(N)_k$ is independently 4-fold degenerate at each position so that, in each probe, $(N)_k$ represents all possible sequences of length k, except that one or more positions in $(N)_k$ may be occupied by a degeneracy-reducing nucleoside. Nucleosides in $(X)_j$ can be identical or different but are not independently selected. In other words, in each probe, $(X)_j$ can only represent a subset of all possible sequences of length j. Thus the identity of one or more nucleotides in $(X)_j$ limits the possible identities for one or more of the other nucleosides. The probes thus contain two portions, of which $(N)_k$ is the unconstrained portion and $(X)_j$ is the constrained portion.

In certain preferred embodiments of the invention the partially constrained probes have the structure 5'-$(X)_j(N)_k$$N_B$*-3' or 3'-$(X)_j(N)_k N_B$*-5', wherein N represents any nucleoside, $N_B$ represents a moiety that is not extendable by ligase, * represents a detectable moiety, $(X)_j$ is a constrained portion of the probe that is at least 2-fold degenerate at each position, nucleosides in $(X)_j$ can be identical or different but are not independently selected, at least one internucleoside linkage is a scissile linkage, j is at least 2, and k is between 1 and 100, with the proviso that a detectable moiety may be present on any nucleoside N or X other than the X at the probe terminus instead of, or in addition to, $N_B$. The scissile linkage can be between two nucleosides in $(X)_j$, between the most distal nucleotide in $(X)_j$ and the most proximal nucleoside in $(N)_k$, between nucleosides within $(N)_k$, or between the terminal nucleoside in $(N)_k$ and $N_B$. Preferably the scissile linkage is a phosphorothiolate linkage.

A plurality of probe families is referred to as a "collection" of probe families. Probes in each probe family in a collection of probe families are labeled with a label that is distinguishable from labels used to label other probe families in the collection. Each probe family preferably has its own defined set of sequences, which optionally do not overlap with any other probe family. Preferably the combination of sets of defined sequences for probe families in a collection of probe families includes all possible sequences of the length of the sequence-determining portion. Preferably a collection of probe families comprises or consists of 4 distinguishably labeled probe families.

Preferably the sequence-determining portions of the probes in each probe family are the same length, and preferably the sequence-determining portions of probe families in a collection of probe families are of the same length. Preferably the sequencing-determining portion is a constrained portion that is at least 2 nucleosides in length.

In some instances, a series of ligation cycles starting from a particular primer allows partial determination of a sequence, i.e., the identification of individual nucleotides spaced apart from one another in a template. Optionally, in order to gather more complete information, a plurality of reactions is performed in which each reaction utilizes a different initializing oligonucleotide i. The initializing oligonucleotides i bind to different portions of the binding region. Preferably the initializing oligonucleotides bind at positions such the extendable termini of the different initializing oligonucleotides are offset by 1 or more nucleotides from each other when hybridized to the template. For example, as shown in FIG. 3, sequencing reactions 1 . . . N are performed. Initializing oligonucleotides $i_1 \ldots i_n$ have the same length and bind such that their terminal nucleotides hybridize to successive adjacent positions in the template. Extension probes $e_1 \ldots e_n$ thus bind at successive adjacent regions of the template and are ligated to the extendable termini of the initializing oligonucleotides. Terminal nucleotide of probe $e_n$ ligated to $i_n$ is complementary to nucleotide of polynucleotide region, i.e., the first unknown polynucleotide in the template. In the second cycle of extension, ligation, and detection, terminal nucleotide of probe $e_{12}$ is complementary to nucleotide of polynucleotide region, i.e., the second nucleotide of unknown sequence. Likewise, terminal nucleotides of extension probes ligated to duplexes initialized with initializing oligonucleotides $i_2$, $i_3$, $i_4$, and so on, will be complementary to the third, fourth, and fifth nucleotides of unknown sequence. It will be appreciated that the initializing oligonucleotides may bind to regions progressively further away from the polynucleotide region rather than progressively closer to it.

The spacer function of the non-terminal nucleotides of the extension probes allows the acquisition of sequence information at positions in the template that are considerably removed from the position at which the initializing oligonucleotide binds without requiring a correspondingly large number of cycles to be performed on any given template.

a. Capping

In any one or more repetitive ligation methods herein, it is possible that fewer than all probes with extendable termini participate in a successful ligation reaction in each cycle of extension, ligation, and cleavage. It will be appreciated that if such probes participated in succeeding cycles, the accuracy of each nucleotide identification step could progressively decline. In certain embodiments of the invention a capping step is included to prevent those extendable termini that do not undergo ligation from participating in future cycles. When sequencing in the 5'→3' direction using extension probes containing a 3'-O—P—S-5' phosphorothiolate linkage, capping may be performed by extending the unligated extendable termini with a DNA polymerase and a non-extendable moiety, e.g., a chain-terminating nucleotide such as a dideoxynucleotide or a nucleotide with a blocking moiety attached, e.g., following the ligation or detection step. When sequencing in the 3'→5' direction using extension probes containing a 3'-S—P—O-5' phosphorothiolate linkage, capping may be performed, e.g., by treating the template with a phosphatase, e.g., following ligation or detection. Other capping methods may also be used.

It is contemplated that any ligation assay or method herein can be highly multiplexed such that a large number of assays (e.g., greater than 1,000) can be performed in parallel, e.g., simultaneously.

Any multiplexed ligation assay can optionally be conducted on solid substrates where one or more ligation reagents (e.g., the ligase, template, probe and/or primer) can be immobilized on a solid support or surface. Optionally, the primers, probe and/or template can be attached to different portions of a solid substrate in the form of an array. Optionally, the template, primer or probe can be covalently attached to the solid substrate.

Optionally, one or more ligation reagents are labeled (e.g., template, probe and/or primer) so that ligation products may be discriminated from each other. Alternatively, ligation products can be distinguished based on: (i) size using electrophoresis or chromatography and/or (ii) detectable labels (Grossman, 1994). For example, multiplexed ligation assays can be conducted on a single sample in a single vessel.

Any of reagents herein (e.g., primer, probe and/or template) can be optionally immobilized on a solid phase. The solid phase optionally comprises a surface to which one or more reactants may be attached electrostatically, hydrophobically, or covalently. Representative solid phases include e.g.: nylon 6; nylon 66; polystyrene; latex beads; magnetic beads; glass beads; polyethylene; polypropylene; polybutylene; butadiene-styrene copolymers; silastic rubber; polyesters; polyamides; cellulose and derivatives; acrylates; methacrylates; polyvinyl; vinyl chloride; polyvinyl chloride; polyvinyl fluoride; copolymers of polystyrene; silica gel; silica wafers glass; agarose; dextrans; liposomes; insoluble protein metals; and, nitrocellulose. Representative solid phases can be formed into appropriate articles such as beads (e.g., microparticles), tubes, strips, disks, filter papers, plates and the like.

In an embodiment, any one of the following can be attached to a solid support (e.g., a bead): the SFL, one or more polynucleotide reagents (e.g., an initializing probe, an extension probe, a target DNA or template, a 3' terminal or 5' terminal polynucleotide).

If so desired, one or more labels can be coupled to any reagent of interest, e.g., the SFL or an antibody that binds specifically to the SFL, one or more polynucleotides (e.g., the template, the 5'-terminal polynucleotide, the 3'-terminal polynucleotide, the template, the initializing probe, the extension probe, etc.

Compositions

Also provided is a polypeptide comprising or consisting essentially of the amino acid sequence of an SFL provided herein, generally provided as GenBank Accession Nos. in the Tables, or a fragment or variant thereof. The fragment or variant thereof preferably can ligate short oligonucleotides at an efficiency comparable to its parent enzyme. Optionally, the variants or fragments of the SFLs are at least 70%, 80, 90%, 95%, 99% identical to the parent SFL. In an example, the SFL is a ligase derived from Hin DNA ligase (e.g., DLX, DLXd or DLXd2) or any fragment or variant thereof that still retains one or more mutant residues shown in FIG. 2, and/or has one or more C-terminal amino acids deleted, e.g., 22 C-terminal amino acids deleted. For example, the mutant Hin DNA ligase is at least 70% identical to Hin D ligase sequence provided in FIG. 2 or in GenBank Accession No. P44121, which ligase comprises an amino acid mutation at position 193 of the Hin D ligase sequence provided in FIG. 2 or in GenBank Accession No. P44121. Optionally the amino acid mutation consists of changing the glycine at position 193 to aspartic acid or glutamic acid.

Also provided is a nucleic acid encoding the novel SFLs or fragments or variants described herein. Also provided are genes of the novel SFL which comprise sequences that direct expression of the SFL. Also provided are nucleic acid vectors comprising a nucleic acid encoding the novel SFL and a host cell comprising such a vector. Also provided is an antibody that can bind specifically to the novel SFL but not to its naturally-occurring parent.

Optionally, the novel SFL or nucleic acid or vector or host cell or antibody is purified, isolated or recombinant.

Also provided is a method of making any one or more ligases described herein comprising: expressing the SFL in a host cell, e.g., by culturing said host cells under conditions such that the ligase is expressed; and optionally recovering or purifying said ligase.

Kits

Also provided are kits comprising components for performing ligation reactions according to the disclosure. Kits can contain an SFL or functional variant or fragment thereof. Kits can alternatively or additionally include one or more oligonucleotide probes less than 12 nucleotides in length, (e.g., less than 8, 7, 6, 5, 4, 3 or 2 nucleotides in length), and/or primer oligonucleotides. In some embodiments, a kit can include CV ligase and one or more oligonucleotides probes less than 6 nucleotides in length. One or more probes for example comprises a 5'-phosphate and/or a label. The label is optionally attached to the 5' terminus, or alternatively to the 3' terminus. Optionally, one or more probes are cleavable.

The kits optionally provide one or more primers, probes and/or templates described herein. The primers and/or probes can have any one or more features or characteristics described herein. For example the probes can comprise a scissile (e.g., phosphorothiolate) linkage. The kits may contain a cleavage reagent suitable for cleaving phosphororothiolate linkages, e.g., AgNO3 and appropriate buffers in which to perform the cleavage. The probes can comprise a trigger residue such as a nucleoside containing a damaged base or an abasic residue. The kits may contain a cleavage reagent suitable for cleaving a linkage between a nucleoside and an adjacent abasic residue and/or a reagent suitable for removing a damaged base from a polynucleotide, e.g., a DNA glycosylase. Certain kits contain oligonucleotide probes that comprise a disaccharide nucleotide and contain periodate as a cleavage reagent. In certain embodiments the kits contain a collection of distinguishably labeled oligonucleotide probe families or collections described herein. Optionally the kit does not comprise a polymerase. Optionally the kit does not comprise an enzyme other than a ligase, phosphatase or kinase. Optionally the kit does not comprise an enzyme other than a SFL that has one or more activities mentioned herein. The kits may include ligation reagents (e.g., ligase, buffers, etc.) and instructions for practicing the particular embodiment of the invention. Appropriate buffers for the other enzymes that may be used, e.g., phosphatase, polymerases, may be included. In some cases, these buffers may be identical. Kits may also include a support, e.g. magnetic beads, which are either pre-attached to primers, primers or templates or are derivatised to be capable of attaching to such molecules. The beads may be functionalized with a primer for performing PCR amplification. Other optional components include washing solutions; vectors for inserting templates for PCR amplification; PCR reagents such as amplification primers, thermostable polymerase, nucleotides; reagents for preparing an emulsion; reagents for preparing a gel, etc. Kits can also comprise a plurality of distinguishably labeled probes, which can be labeled such that the identity of the label provides information about the sequence of the probe. Kits can also comprise other or additional compositions or reagents for use in ligation sequencing determination protocol. Optionally, the identity of the label provides the exact identity of a nucleotide occupying one degenerate position in the probe. For example, the identity of the label optionally eliminates one or more combinations or permutations of nucleotides at two or more degenerate positions. The probes are for example degenerate at two or more constrained positions, where the identity of a nucleotide at one constrained position eliminates at least one possible identity of a nucleotide at another constrained position. Optionally, knowing the identity of a constrained residue in that probe further eliminates at least one possible identity for another constrained residue in the probe.

Unless otherwise apparent from the context, any feature can be claimed in combination with any other, or be claimed as not present in combination with another feature. A feature can be for example any variation, step, feature, property, composition, method, step, degree, level, component, material, substance, element, mode, variable, aspect, measure, amount or embodiment.

Many features described herein are intended to be optional. If any feature is not explicitly indicated as being necessary, it is to be regarded as optional. Non-limiting examples of language indicating that a feature is optional include terms such as "variation," "where," "while," "when," "optionally," "include," "preferred," "especial," "recommended," "advisable," "particular," "should," "alternative," "typical," "representative," "various," "such as," "the like," "can," "may," "example," "embodiment," or "in an aspect" or "if" or any combination and/or variation of such terms.

Any indication that a feature is optional is intended to provide adequate support for claims that include closed or exclusive or negative language (e.g., under 35 U.S.C. 112 or Art. 83 and 84 of EPC). Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can be X, such language is intended to provide support for a claim that explicitly specifies that A is not X.

Non-limiting examples exclusive or negative terms include "only," "solely," "consisting of," "consisting essentially of," "alone," "without", "in the absence of (e.g., other items of the same type, structure and/or function)" "excluding," "not", "doesn't", "cannot," or any combination and/or variation of such language.

Similarly, referents such as "a," "an," "said," or "the," are intended to support explicitly single or plural referents where so desired. Non-limiting examples of plural referents include "at least one," "one or more," "more than one," "two or more," "a multiplicity," "a plurality," "any combination of," "any permutation of," "any one or more of," etc.

All publications and patents cited in this specification are herein incorporated by reference as if each individual publication or patent were specifically and individually indicated to be incorporated by reference. Genbank records referenced by Genbank ID or accession number, particularly any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

The following examples are provided for illustrative purposes and are not intended to limit the invention.

EXAMPLES

Example 1

This example describes ligation of short probes.

The oligonucleotide reagents were as follows. The short oligos in forward ligation (i.e., ligation of the 3' terminus of the probe to the 5' terminus of the primer) were: 8mer: 5'-CTCATTCG-3'; 6mer: 5'-TCATTCG-3' 5mer: 5'-ATTCG-3'; 4mer: 5'-TTCG-3'; 3mer: 5'-TCG-3'. Short oligos used for reverse ligation (i.e., ligation of the 5' terminus of the probe to the 3' terminus of the primer) were the same as forward ligation oligos except they have a 5' phosphate. All oligonucleotides were obtained from Integrated DNA Technologies. The forward primer was: PO4-5'-CTGCTGTAC-CGTACATCCGC-3'-6FAM. The reverse primer was: 5'-FAM-CTGCCCCGGGTTCCTCATTCTCT-3'

Ligase Substrate Preparation: MyOne magnetic beads labeled with carboxylic acid, were obtained from Invitrogen. 5' amino labeled, 41-base oligonucleotide (CCA CTA CGC CTC CGC TTT CCT CTC TAT GGG CAG TCG GTG AT) was coupled to MyOne beads using standard amine coupling chemistry as taught in Nakajima et al., Bioconjugate Chem. 1995, 6(1),123-130 (FIG. 1b). PCR was used to extend this oligonucleotide using (CTG CCC CGG GTT CCT CAT TCT CTA TTC GCT GCT GTA CCG TAC ATC CGC CTT GGC CGT ACA GCA GAT CAC CGA CTG CCC ATA GAG AGG). The following 105 base ligation substrate was now tethered to MyOne beads (CCA CTA CGC CTC CGC TTT CCT CTC TAT GGG CAG TCG GTG ATC TGC TGT ACG GCC AAG GCG GAT GTA CGG TAC AGC AGC GAA TAG AGA ATG AGG AAC CCG GGG CAG, FIG. 1a). The amount of 105-base oligo tethered to the bead was measured by hybridization of a fluorescently labeled "primer" oligo, with 3' fluorescein label (6FAM) for detection by capillary electrophoresis. The amount of fluorescence denatured from the template was compared to a standard curve.

Ligation reactions were performed in buffer containing 50 mM Tris-HCl, 10 mM MgCL2, 1 mM ATP, 1 mM DTT and 5% w/v PEG 8000 at pH 7.5 (ligase buffer). Primer oligonucleotide was annealed to template in ligase buffer by heating to 85° C. for 10 minutes followed by slow cooling to room temperature. In the case of forward ligation, the primer was 5' phosphorylated and a 3' 6FAM labeled. In the case of reverse ligation, the primer was 5' 6FAM labeled. Ligation reactions were performed in a 96 well plate using 2 nM template/primer, 2.0 µM ligase, 2-5 µM short oligonucleotide in a total volume of 50 µL. The ligation reactions proceeded for 20 minutes at 15° C. The reactions were stopped using 1% v/v SDS followed by magnetic separation of the templated beads from the solution. Beads were washed three times in 100 µL of 1% SDS prior to washing with 100 uL of 100% formamide. 5 µL of the supernatant containing denatured, FAM labeled primer and ligation product were then analyzed by capillary electrophoresis. The ligation efficiency was calculated as the ratio of peak areas determined by CE, where FAM labeled, unligated and ligated primer were separated, i.e., Efficiency=ligated/(ligated+unligated).

Shown in FIGS. 3-5 are a series of ligations of probes of different lengths with a variety of SFLs. In each panel, the ligation reaction is plotted as a function of the probe length. These data clearly demonstrate that small footprint ligases can ligate probe substrates as short as two nucleotides. By utilizing SFLs, the size of a sequencing probe set (e.g., for ligation sequencing in SOLiD™) can be reduced from the current set of 1024 8-mers to as few as 16 (in the case of di-mers), 64 (in the case of trimers), or 256 in the case of tetramers.

In another experiment, the ligation efficiency of SF Ligase was compared using the same experimental system as above to T4 DNA ligase, using 8-mer ligation sequencing probes that were conjugated or not conjugated to dyes. SFL the highest overall ligation efficiency for both the dark (chase) probe and the labeled sequencing probe. This is true at the 200 nM concentration of probe, which is currently used in SOLiD. Specifically, a mixture of 1024 probes is used in SOLiD, where each individual probe of the 1024 probes is present at a final working concentration of 200 nM. The other concentrations were 2000 nM of enzyme and 1 nM bead template, where ligation was performed at 15° C. for 30 minutes. Results are shown in Table 2.

TABLE 2

| Maximum ligation efficiency of 8mer probes by various ligase enzymes | | |
|---|---|---|
| Ligase | Dark | Cy 5 |
| SFL | 0.91 ± 0.01 | 0.82 ± 0.01 |
| T4 | 0.67 ± 0.02 | 0.62 ± 0.02 |

Example 2

The fidelity of a small-footprint ligase (CV ligase) was determined to be surprisingly better than T4 DNA ligase in DNA sequencing by ligation on the SOLiD sequencing system. A 35-nucleotide DNA template was covalently attached to beads, such each magnetic bead had about 100,000 covalently bound DNA molecules on average. Approximately 40 million beads were subjected to a ligation sequencing reaction at 20° C. The sequencing reaction ligated 8-mer oligonucleotide "probes" labeled with fluorescent dye onto a primer, and a total of seven consecutive ligation or probing events were performed on each template molecule. The approximate number of ligation events were therefore 100,000 (i.e., number of template molecules per bead)×40,000,000 (i.e., number of beads)×7 (number of ligation events per template)=$2.8 \times 10^{13}$.

Results are given in Table 3 below. 0MM=Percentage of all ligation products (which are the result of seven consecutive ligation events) with no mismatches; 3MM=Percentage of all ligation products (which are the result of seven consecutive ligation events) with less than 3 mismatches.

TABLE 3

| Ligase | 0MM | 3MM |
|---|---|---|
| T4 | 20% | 57% |
| SF | 27% | 65% |

The sequencing by ligation data demonstrates that 20% of the time the ligation product was perfectly complementary to the template and formed by seven consecutive ligation events that were all correct. An estimate of the ligation fidelity (expressed as the percentage probability that a ligation event is correct, or "p") can be calculated from the equation: 0MM rate=$(p/100)^n$ where p is the percentage ligation fidelity and n is the number of ligation events per final ligation product (here, seven). Thus for T4 DNA ligase, the ligation fidelity is 79.5% and for SFL the ligation fidelity is 83%.

---

We claim:

1. A method of template-dependent ligation, said method comprising:
   a. enzymatically ligating a proximal terminus of a first oligonucleotide and a proximal terminus of a second oligonucleotide, wherein the proximal termini of the first and the second oligonucleotides are adjacently hybridized to a template to form a ligation product, wherein the ligation is performed by a Chlorella Virus ligase (CV ligase), wherein the first oligonucleotide and/or second oligonucleotide is less than 8 nucleotides in length, wherein the first oligonucleotide hybridizes to a region on the template adjacent to the proximal terminus of the second oligonucleotide, and wherein the first oligonucleotide is fluorescently labeled, wherein the first oligonucleotide comprises a proximal portion that is (i) perfectly hybridized to the template and is (ii) L nucleotides long, wherein the first oligonucleotide's L+1th nucleotide is mismatched with the template; and
   b. detecting the fluorescent label of the first oligonucleotide that has ligated to the second oligonucleotide.

2. The method of claim 1, wherein the effiency of the ligation is at least 80%.

3. The method of claim 1, wherein the proximal terminus of the first oligonucleotide is its 3' terminus and the proximal terminus of the second oligonucleotide is its 5'terminus.

4. The method of claim 1, wherein the proximal terminus of the first oligonucleotide is its 5' terminus and the proximal terminus of the second oligonucleotide is its 3'terminus.

5. The method of claim 1, wherein the second oligonucleotide and/or template is fluorescently labeled.

6. A method of claim 1, wherein at least one of the first oligonucleotide, the template, and/or the second oligonucleotide is immobilized.

7. The method of claim 1, wherein ligation is performed in the presence of a multiplicity of additional oligonucleotides that are at least partially complementary to the same region on the templae as the first oligonucleotide.

8. The method of claim 7, wherein at least one of the multiplicity of additional oligonucleotides is labeled distinguishably from the first oligonucleotide.

9. The method of claim 7, wherein the portion of the second oligonucleotide that is hybridized to the template is 2 to 20 nucleotides in length.

10. The method of claim 1, wherein the ligation is repeated at least once.

11. The method of claim 10, any ligation product of a previous ligation reaction is used as the second oligonucleotide of a next ligation.

12. The method of claim 10, further comprising detecting whether the first oligonucleotide has ligated to the second oligonucleotide before repeating the ligation.

13. The method of claim 10, wherein any ligation product of the previous ligation reaction is used as the template of the next ligation reaction.

14. The method of claim 1, wherein the method comprises a ligase chain reaction.

15. The method of claim 1, wherein the first oligonucleotide serces a probe function.

16. The method of claim 1, wherein the second oligonucleotide serves a primer function.

17. The method of claim 1, wherein the second oligonucleotide is extendable at its 3' terminus.

18. A method of template-dependent ligation, said method comprising:
   a. enzymatically ligating a first oligonucleotide and a second oligonucleotide, wherein said first oligonucleotide and said second oligonucleotide are hybridized to an RNA template, to form a ligation product, wherein the ligation is performed by a Chlorella Virus ligase (CV ligase), wherein the portion of the first oligonucleotide that is hybridized to the RNA template is 2 to 8 nucleotides in length and the portion of the second oligonucleotide that is hybridized to the RNA template is 2 to 20 nucleotides in length, wherein the first oligonucleotide is at least partially complementary to a region on the RNA template adjacent to the proximal terminus of the second oligonucleotide, and wherein the first oligonucleotide is labeled;
   b. amplifying the ligation product; and
   c. detecting the label of the amplified ligation product.

19. The method of claim 18, wherein the efficiency of the ligation is atleast 80%.

20. The method of claim 18, wherein the label is a fluorescent label.

21. The method of claim 18, wherein the RNA template is an miRNA template.

22. The method of claim 18, wherein the amplifying is performed by a polymerase chain reaction (PCR).

* * * * *

SEQUENCE LISTING

```
<160> NUMBER OF SEQ ID NOS: 87

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gcggatgtac ggtacagcag                                                      20

<210> SEQ ID NO 2
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
agtcggtgat                                                                 10

<210> SEQ ID NO 3
<211> LENGTH: 298
<212> TYPE: PRT
<213> ORGANISM: Paramecium bursaria Chlorella virus 1

<400> SEQUENCE: 3

Met Ala Ile Thr Lys Pro Leu Leu Ala Ala Thr Leu Glu Asn Ile Glu
1               5                   10                  15

Asp Val Gln Phe Pro Cys Leu Ala Thr Pro Lys Ile Asp Gly Ile Arg
            20                  25                  30

Ser Val Lys Gln Thr Gln Met Leu Ser Arg Thr Phe Lys Pro Ile Arg
        35                  40                  45

Asn Ser Val Met Asn Arg Leu Leu Thr Glu Leu Leu Pro Glu Gly Ser
    50                  55                  60

Asp Gly Glu Ile Ser Ile Glu Gly Ala Thr Phe Gln Asp Thr Thr Ser
65                  70                  75                  80

Ala Val Met Thr Gly His Lys Met Tyr Asn Ala Lys Phe Ser Tyr Tyr
                85                  90                  95

Trp Phe Asp Tyr Val Thr Asp Asp Pro Leu Lys Lys Tyr Ile Asp Arg
            100                 105                 110

Val Glu Asp Met Lys Asn Tyr Ile Thr Val His Pro His Ile Leu Glu
        115                 120                 125

His Ala Gln Val Lys Ile Ile Pro Leu Ile Pro Val Glu Ile Asn Asn
    130                 135                 140

Ile Thr Glu Leu Leu Gln Tyr Gly Arg Asp Val Leu Ser Lys Gly Phe
145                 150                 155                 160

Glu Gly Val Met Ile Arg Lys Pro Asp Gly Lys Tyr Lys Phe Gly Arg
                165                 170                 175
```

```
Ser Thr Leu Lys Glu Gly Ile Leu Lys Met Lys Gln Phe Lys Asp
            180                 185                 190

Ala Glu Ala Thr Ile Ile Ser Met Thr Ala Leu Phe Lys Asn Thr Asn
            195                 200                 205

Thr Lys Thr Lys Asp Asn Phe Gly Tyr Ser Lys Arg Ser Thr His Lys
            210                 215                 220

Ser Gly Lys Val Glu Glu Asp Val Met Gly Ser Ile Glu Val Asp Tyr
225                 230                 235                 240

Asp Gly Val Val Phe Ser Ile Gly Thr Gly Phe Asp Ala Asp Gln Arg
                245                 250                 255

Arg Asp Phe Trp Gln Asn Lys Glu Ser Tyr Ile Gly Lys Met Val Lys
            260                 265                 270

Phe Lys Tyr Phe Glu Met Gly Ser Lys Asp Cys Pro Arg Phe Pro Val
            275                 280                 285

Phe Ile Gly Ile Arg His Glu Glu Asp Arg
            290                 295

<210> SEQ ID NO 4
<211> LENGTH: 306
<212> TYPE: PRT
<213> ORGANISM: Burkholderia pseudomallei

<400> SEQUENCE: 4

Met Ser Gly Val Pro Tyr Gly Phe Lys Pro Asn Leu Ala Ala Thr Leu
1               5                   10                  15

Thr Lys Pro Glu Leu Ile Lys Phe Pro Val Trp Ala Ser Pro Lys Ile
            20                  25                  30

Asp Gly Ile Arg Cys Val Phe Phe Gly Gly Val Ala Tyr Ser Arg Ser
        35                  40                  45

Leu Lys Pro Ile Pro Asn Pro Val Val Gln Glu Phe Ala Lys Ala Tyr
50                  55                  60

Ala Asn Leu Leu Glu Gly Leu Asp Gly Glu Leu Thr Val Gly Ser Pro
65                  70                  75                  80

Thr Asp Ala Asn Cys Met Gln Asn Ser Met Ala Val Met Ser Lys Ala
                85                  90                  95

Ala Ala Pro Asp Phe Thr Phe His Val Phe Asp Trp Phe His Pro Ala
            100                 105                 110

Gln Ala His Ile Glu Phe Trp Gln Arg Ser Asp Val Val Glu Asp Arg
        115                 120                 125

Ile Val Gln Phe Tyr Asp Arg Tyr Pro Glu Val Asp Ile Arg Ala Ala
    130                 135                 140

Pro Gln Val Leu Cys Thr Ser Leu Ala His Leu Asp Thr Asn Glu Ala
145                 150                 155                 160

Arg Trp Leu Ala Asp Gly Tyr Glu Gly Met Met Ile Arg Asp His Cys
                165                 170                 175

Gly Arg Tyr Lys Phe Gly Arg Ser Thr Glu Arg Glu Gly Gly Leu Val
            180                 185                 190

Lys Val Lys Arg Phe Thr Asp Ala Glu Ala Ile Val Ile Gly Phe Glu
        195                 200                 205

Glu Glu Met His Asn Ala Asn Glu Ala Lys Arg Asp Ala Thr Gly Arg
    210                 215                 220

Thr Glu Arg Ser Thr Ser Lys Ala Gly Leu His Gly Lys Gly Thr Leu
225                 230                 235                 240

Gly Ala Leu Val Val Lys Asn Glu Arg Gly Ile Val Phe Asn Ile Gly
                245                 250                 255
```

Thr Gly Phe Thr Ala Ala Gln Arg Ala Asp Tyr Trp Ala Asn His Pro
        260                 265                 270

Ser Leu Phe Gly Lys Met Val Lys Phe Lys His Phe Asp His Gly Thr
            275                 280                 285

Val Asp Ala Pro Arg His Pro Val Phe Ile Gly Phe Arg His Pro Glu
290                 295                 300

Asp Met
305

<210> SEQ ID NO 5
<211> LENGTH: 268
<212> TYPE: PRT
<213> ORGANISM: Haemophilus influenza

<400> SEQUENCE: 5

Met Lys Phe Tyr Arg Thr Leu Leu Leu Phe Ala Ser Ser Phe Ala
1               5                   10                  15

Phe Ala Asn Ser Asp Leu Met Leu Leu His Thr Tyr Asn Asn Gln Pro
            20                  25                  30

Ile Glu Gly Trp Val Met Ser Glu Lys Leu Asp Gly Val Arg Gly Tyr
        35                  40                  45

Trp Asn Gly Lys Gln Leu Leu Thr Arg Gln Gly Gln Arg Leu Ser Pro
    50                  55                  60

Pro Ala Tyr Phe Ile Lys Asp Phe Pro Pro Phe Ala Ile Asp Gly Glu
65                  70                  75                  80

Leu Phe Ser Glu Arg Asn His Phe Glu Glu Ile Ser Thr Ile Thr Lys
                85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Ile Glu Gln
    130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190

Gly Glu Glu Cys Thr Val Ile Ala His His Lys Gly Lys Gly Gln Phe
        195                 200                 205

Glu Asn Val Met Gly Ala Leu Thr Cys Lys Asn His Arg Gly Glu Phe
    210                 215                 220

Lys Ile Gly Ser Gly Phe Asn Leu Asn Glu Arg Glu Asn Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265

<210> SEQ ID NO 6
<211> LENGTH: 268
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 6

```
Met Lys Phe Tyr Arg Thr Leu Leu Leu Phe Ala Ser Ser Phe Ala
1               5                   10                  15

Phe Ala Asn Ser Asp Leu Met Leu His Thr Tyr Asn Asn Gln Pro
            20                  25                  30

Ile Glu Gly Trp Val Met Ser Glu Lys Leu Asp Gly Val Arg Gly Tyr
        35                  40                  45

Trp Asn Gly Lys Gln Leu Leu Thr Arg Gln Gly Gln Arg Leu Ser Pro
50                  55                  60

Pro Ala Tyr Phe Ile Lys Asp Phe Pro Phe Ala Ile Asp Gly Glu
65                  70                  75                  80

Leu Phe Ser Glu Arg Asn His Phe Glu Glu Ile Ser Ser Ile Thr Lys
                85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Glu Gln
130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190

Gly Glu Glu Cys Thr Val Ile Ala His His Lys Gly Lys Gly Gln Phe
        195                 200                 205

Glu Asn Val Met Gly Ala Leu Thr Cys Lys Asn His Arg Gly Glu Phe
210                 215                 220

Lys Ile Gly Ser Gly Phe Asn Leu Asn Glu Arg Glu Asn Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265
```

<210> SEQ ID NO 7
<211> LENGTH: 268
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 7

```
Met Lys Phe Tyr Arg Thr Leu Leu Leu Phe Ala Ser Ser Phe Ala
1               5                   10                  15

Phe Ala Asn Ser Asp Leu Met Leu His Thr Tyr Asn Asn Gln Pro
            20                  25                  30

Ile Glu Gly Trp Val Met Ser Glu Lys Leu Asp Gly Val Arg Gly Tyr
        35                  40                  45

Trp Asn Gly Lys Gln Leu Leu Thr Arg Gln Gly Gln Arg Leu Ser Pro
50                  55                  60
```

```
Pro Ala Tyr Phe Ile Lys Asp Phe Pro Pro Phe Ala Ile Asp Gly Glu
 65                  70                  75                  80

Leu Phe Ser Glu Arg Asn His Phe Glu Glu Ile Ser Ser Ile Thr Lys
                 85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Ile Glu Gln
130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190

Asp Glu Glu Cys Thr Val Ile Ala His His Lys Gly Lys Gly Gln Phe
        195                 200                 205

Glu Asn Val Met Gly Ala Leu Thr Cys Lys Asn His Arg Gly Glu Phe
210                 215                 220

Lys Ile Gly Ser Gly Phe Asn Leu Asn Glu Arg Glu Asn Pro Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265

<210> SEQ ID NO 8
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Leu Leu His Thr Tyr Asn Asn Gln Pro Ile Glu Gly Trp Val Met
 1               5                  10                  15

Ser Glu Lys Leu Asp Gly Val Arg Gly Tyr Trp Asn Gly Lys Gln Leu
                20                  25                  30

Leu Thr Arg Gln Gly Gln Arg Leu Ser Pro Pro Ala Tyr Phe Ile Lys
             35                  40                  45

Asp Phe Pro Pro Phe Ala Ile Asp Gly Glu Leu Phe Ser Glu Arg Asn
 50                  55                  60

His Phe Glu Glu Ile Ser Ser Ile Thr Lys Ser Phe Lys Gly Asp Gly
 65                  70                  75                  80

Trp Glu Lys Leu Lys Leu Tyr Val Phe Asp Val Pro Asp Ala Glu Gly
                 85                  90                  95

Asn Leu Phe Glu Arg Leu Ala Lys Leu Lys Ala His Leu Leu Glu His
            100                 105                 110

Pro Thr Thr Tyr Ile Glu Ile Ile Glu Gln Ile Pro Val Lys Asp Lys
        115                 120                 125

Thr His Leu Tyr Gln Phe Leu Ala Gln Val Glu Asn Leu Gln Gly Glu
130                 135                 140
```

```
Gly Val Val Arg Asn Pro Asn Ala Pro Tyr Glu Arg Lys Arg Ser
145                 150                 155                 160

Ser Gln Ile Leu Lys Leu Lys Thr Ala Arg Asp Glu Glu Cys Thr Val
                165                 170                 175

Ile Ala His His Lys Gly Lys Gly Gln Phe Glu Asn Val Met Gly Ala
                180                 185                 190

Leu Thr Cys Lys Asn His Arg Gly Glu Phe Lys Ile Gly Ser Gly Phe
                195                 200                 205

Asn Leu Asn Glu Arg Glu Asn Pro Pro Ile Gly Ser Val Ile Thr
            210                 215                 220

Tyr Lys Tyr Arg Gly Ile Thr Asn Ser Gly Lys Pro Arg Phe Ala Thr
225                 230                 235                 240

Tyr Trp Arg Glu Lys Lys
                245

<210> SEQ ID NO 9
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 9

Lys Xaa Asp Gly Xaa Arg
1               5

<210> SEQ ID NO 10
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 10

Ala Thr Pro Lys Ile Asp Gly Ile Arg
1               5

<210> SEQ ID NO 11
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 11

Glu Gly Ser Asp Gly Glu Ile Ser
1               5

<210> SEQ ID NO 12
<211> LENGTH: 5
<212> TYPE: PRT
<213> ORGANISM: Unknown
```

```
<220> FEATURE:
<221> NAME/KEY: source
<223> OTHER INFORMATION: /note="Description of Unknown: Ligase motif
      peptide"

<400> SEQUENCE: 12

Tyr Trp Phe Asp Tyr
1               5

<210> SEQ ID NO 13
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 13

Glu Gly Val Met Ile Arg
1               5

<210> SEQ ID NO 14
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 14

Leu Leu Lys Met Lys
1               5

<210> SEQ ID NO 15
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 15

Cys Glu Leu Lys Leu Asp Gly Leu Ala
1               5

<210> SEQ ID NO 16
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 16

Val Glu His Lys Val Asp Gly Leu Ser
1               5

<210> SEQ ID NO 17
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"
```

```
<400> SEQUENCE: 17

Cys Glu Pro Lys Leu Asp Gly Leu Ala
1               5

<210> SEQ ID NO 18
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 18

Cys Glu Leu Lys Leu Asp Gly Val Ala
1               5

<210> SEQ ID NO 19
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 19

Ala Glu Ile Lys Tyr Asp Gly Val Arg
1               5

<210> SEQ ID NO 20
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 20

Cys Glu Tyr Lys Tyr Asp Gly Gln Arg
1               5

<210> SEQ ID NO 21
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 21

Val Asp Tyr Lys Tyr Asp Gly Glu Arg
1               5

<210> SEQ ID NO 22
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 22

Phe Glu Ile Lys Tyr Asp Gly Ala Arg
```

```
<210> SEQ ID NO 23
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 23

Phe Glu Gly Lys Trp Asp Gly Tyr Arg
1               5

<210> SEQ ID NO 24
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 24

Ala Arg Glu Lys Ile His Gly Thr Asn
1               5

<210> SEQ ID NO 25
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 25

Ala Cys Glu Lys Val His Gly Thr Asn
1               5

<210> SEQ ID NO 26
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 26

Ile Leu Thr Lys Glu Asp Gly Ser Leu
1               5

<210> SEQ ID NO 27
<211> LENGTH: 9
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 27

Val Glu Glu Lys Val Asp Gly Tyr Asn
1               5

<210> SEQ ID NO 28
```

```
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 28

Leu Glu Val Arg Gly Glu Val Phe
1               5

<210> SEQ ID NO 29
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 29

Val Glu Val Arg Gly Glu Cys Tyr
1               5

<210> SEQ ID NO 30
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 30

Leu Glu Val Arg Gly Glu Val Tyr
1               5

<210> SEQ ID NO 31
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 31

Leu Glu Ala Arg Gly Glu Ala Phe
1               5

<210> SEQ ID NO 32
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 32

Phe Met Leu Asp Gly Glu Leu Met
1               5

<210> SEQ ID NO 33
<211> LENGTH: 8
<212> TYPE: PRT
<213> ORGANISM: Unknown
<220> FEATURE:
```

```
<221> NAME/KEY: source
<223> OTHER INFORMATION: /note="Description of Unknown: Ligase motif
      peptide"

<400> SEQUENCE: 33

Phe Ile Leu Asp Thr Glu Ala Val
1               5

<210> SEQ ID NO 34
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 34

Phe Ile Ile Glu Gly Glu Ile Val
1               5

<210> SEQ ID NO 35
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 35

Ala Ile Val Glu Gly Glu Leu Val
1               5

<210> SEQ ID NO 36
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 36

Val Val Leu Asp Gly Glu Ala Val
1               5

<210> SEQ ID NO 37
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 37

Tyr Gln Val Phe Gly Glu Phe Ala
1               5

<210> SEQ ID NO 38
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"
```

```
<400> SEQUENCE: 38

Leu Val Leu Asn Gly Glu Leu Phe
1               5

<210> SEQ ID NO 39
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 39

Phe Thr Ala Asn Phe Glu Phe Val
1               5

<210> SEQ ID NO 40
<211> LENGTH: 8
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 40

Leu Ile Leu Val Gly Glu Met Ala
1               5

<210> SEQ ID NO 41
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 41

Phe Cys Tyr Gly Val
1               5

<210> SEQ ID NO 42
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 42

Phe Leu Tyr Thr Val
1               5

<210> SEQ ID NO 43
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 43

Thr Phe Tyr Ala Leu
1               5
```

-continued

```
<210> SEQ ID NO 44
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 44

Ile Cys His Gly Leu
1               5

<210> SEQ ID NO 45
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 45

Asn Ala Tyr Gly Ile
1               5

<210> SEQ ID NO 46
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 46

Phe Val Tyr Gly Leu
1               5

<210> SEQ ID NO 47
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 47

Lys Leu Tyr Ala Ile
1               5

<210> SEQ ID NO 48
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 48

Tyr Ala Phe Asp Ile
1               5

<210> SEQ ID NO 49
<211> LENGTH: 5
```

```
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 49

Phe Leu Phe Asp Leu
1               5

<210> SEQ ID NO 50
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 50

Asn Leu Phe Asp Val
1               5

<210> SEQ ID NO 51
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 51

Trp Ala Phe Asp Leu
1               5

<210> SEQ ID NO 52
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 52

Tyr Val Phe Asp Ile
1               5

<210> SEQ ID NO 53
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 53

Phe Ala Phe Asp Ile
1               5

<210> SEQ ID NO 54
<211> LENGTH: 5
<212> TYPE: PRT
<213> ORGANISM: Unknown
<220> FEATURE:
<221> NAME/KEY: source
```

```
<223> OTHER INFORMATION: /note="Description of Unknown: Ligase motif
      peptide"

<400> SEQUENCE: 54

Ile Leu Leu Asn Ala
1               5

<210> SEQ ID NO 55
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 55

Phe Leu Phe Asp Val
1               5

<210> SEQ ID NO 56
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 56

Asp Gly Val Val Ile Lys
1               5

<210> SEQ ID NO 57
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 57

Asp Gly Ile Val Ile Lys
1               5

<210> SEQ ID NO 58
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 58

Asp Gly Val Val Val Lys
1               5

<210> SEQ ID NO 59
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 59
```

```
Asp Gly Thr Val Leu Lys
1               5

<210> SEQ ID NO 60
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 60

Glu Gly Leu Ile Val Lys
1               5

<210> SEQ ID NO 61
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 61

Glu Gly Leu Met Val Lys
1               5

<210> SEQ ID NO 62
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 62

Glu Gly Val Met Val Lys
1               5

<210> SEQ ID NO 63
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 63

Glu Gly Leu Met Ala Lys
1               5

<210> SEQ ID NO 64
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 64

Glu Gly Val Ile Ala Lys
1               5
```

```
<210> SEQ ID NO 65
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 65

Glu Gly Tyr Val Leu Lys
1               5

<210> SEQ ID NO 66
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 66

Glu Gly Val Val Ile Arg
1               5

<210> SEQ ID NO 67
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 67

Glu Gly Tyr Val Ala Val
1               5

<210> SEQ ID NO 68
<211> LENGTH: 6
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 68

Glu Gly Ile Ile Met Lys
1               5

<210> SEQ ID NO 69
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 69

Ala Val Ala Phe Lys
1               5

<210> SEQ ID NO 70
<211> LENGTH: 5
<212> TYPE: PRT
```

```
<213> ORGANISM: Unknown
<220> FEATURE:
<221> NAME/KEY: source
<223> OTHER INFORMATION: /note="Description of Unknown: Ligase motif
      peptide"

<400> SEQUENCE: 70

Ala Ile Ala Tyr Lys
1               5

<210> SEQ ID NO 71
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 71

Ala Leu Ala Tyr Lys
1               5

<210> SEQ ID NO 72
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 72

Trp Trp Lys Met Lys
1               5

<210> SEQ ID NO 73
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 73

Trp Leu Lys Leu Lys
1               5

<210> SEQ ID NO 74
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 74

Trp Ile Lys Leu Lys
1               5

<210> SEQ ID NO 75
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
``` peptide"

<400> SEQUENCE: 75

Trp Leu Lys Ile Lys
1               5

<210> SEQ ID NO 76
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 76

Trp Val Lys Asp Lys
1               5

<210> SEQ ID NO 77
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 77

Ala Ile Lys Cys Lys
1               5

<210> SEQ ID NO 78
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 78

Ile Ile Lys Leu Arg
1               5

<210> SEQ ID NO 79
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 79

His Phe Lys Ile Lys
1               5

<210> SEQ ID NO 80
<211> LENGTH: 5
<212> TYPE: PRT
<213> ORGANISM: Unknown
<220> FEATURE:
<221> NAME/KEY: source
<223> OTHER INFORMATION: /note="Description of Unknown: Ligase motif
      peptide"

<400> SEQUENCE: 80

```
Ile Val Lys Tyr Val
1               5
```

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
ctgctgtacc gtacatccgc                                              20

<210> SEQ ID NO 82
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
ctgccccggg ttcctcattc tct                                          23

<210> SEQ ID NO 83
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
ccactacgcc tccgctttcc tctctatggg cagtcggtga t                      41

<210> SEQ ID NO 84
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
ctgccccggg ttcctcattc tctattcgct gctgtaccgt acatccgcct tggccgtaca   60
gcagatcacc gactgcccat agagagg                                      87

<210> SEQ ID NO 85
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
ccactacgcc tccgctttcc tctctatggg cagtcggtga tctgctgtac ggccaaggcg   60
gatgtacggt acagcagcga atagagaatg aggaacccgg ggcag                  105

<210> SEQ ID NO 86

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
gcggatgtac ggtacagcag cgaataga                                      28

<210> SEQ ID NO 87
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
gcccatagag agga                                                     14
```